United States Patent
Fukumoto et al.

(10) Patent No.: US 10,179,350 B2
(45) Date of Patent: Jan. 15, 2019

(54) CLEANING DEVICE

(71) Applicant: Sharp Kabushiki Kaisha, Osaka-shi, Osaka (JP)

(72) Inventors: Shohei Fukumoto, Yao (JP); Hiroaki Yamamoto, Yao (JP); Kohichi Tamura, Yao (JP); Kohichi Nakamura, Yao (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 413 days.

(21) Appl. No.: 14/777,756

(22) PCT Filed: Jun. 19, 2014

(86) PCT No.: PCT/JP2014/066269
§ 371 (c)(1),
(2) Date: Sep. 17, 2015

(87) PCT Pub. No.: WO2015/012030
PCT Pub. Date: Jan. 29, 2015

(65) Prior Publication Data
US 2016/0271652 A1    Sep. 22, 2016

(30) Foreign Application Priority Data

Jul. 24, 2013  (JP) ................................. 2013-153935
Oct. 4, 2013   (JP) ................................. 2013-209244

(51) Int. Cl.
*A61B 90/70*   (2016.01)
*B01F 3/04*    (2006.01)
(Continued)

(52) U.S. Cl.
CPC ............ *B08B 3/02* (2013.01); *B01F 3/04503* (2013.01); *B01F 5/043* (2013.01); *B01F 5/0426* (2013.01);
(Continued)

(58) Field of Classification Search
CPC .......... A61B 2090/701; B01F 3/04503; B01F 5/0426; B01F 5/0428; B01F 5/043;
(Continued)

(56) References Cited

U.S. PATENT DOCUMENTS

2012/0276474 A1    11/2012   Yamauchi et al.
2014/0230848 A1    8/2014    Yamauchi et al.
2015/0027502 A1    1/2015    Yamamoto et al.

FOREIGN PATENT DOCUMENTS

JP    05-192064 A    8/1993
JP    2007-160175 A  6/2007
(Continued)

OTHER PUBLICATIONS

Official Communication issued in International Patent Application No. PCT/JP2014/066269, dated Sep. 16, 2014.

*Primary Examiner* — Levon J Shahinian
(74) *Attorney, Agent, or Firm* — Keating & Bennett, LLP

(57) ABSTRACT

A cleaning device (100) according to the present invention is constituted by including in a cleaning nozzle member (21) provided inside a cleaning tank (2): a large pipe diameter part (211) that supplies a cleaning fluid (31) pressure-fed from a retention tank (3); a small pipe diameter part (212) that increases the speed of a flow rate for the cleaning fluid (31) flowing in the large pipe diameter part; a conical pipe diameter part (213) that generates a fluid that includes minute bubbles by cavitation; and a guide pipe diameter part (214) for accommodating an object (5) to be cleaned. The cleaning fluid (31) is ejected to the entirety of the object (5).

14 Claims, 13 Drawing Sheets

(51) Int. Cl.
*B01F 5/04* (2006.01)
*B05B 7/04* (2006.01)
*B08B 3/02* (2006.01)
*B08B 3/08* (2006.01)
*B08B 3/10* (2006.01)
*B08B 3/12* (2006.01)
*B08B 5/00* (2006.01)

(52) U.S. Cl.
CPC .......... *B01F 5/0428* (2013.01); *B05B 7/0483* (2013.01); *B08B 3/08* (2013.01); *B08B 3/10* (2013.01); *B08B 3/102* (2013.01); *B08B 3/12* (2013.01); *B08B 5/00* (2013.01); *A61B 2090/701* (2016.02); *B01F 2005/0438* (2013.01)

(58) Field of Classification Search
CPC . B01F 2005/0438; B05B 7/0483; B08B 3/02; B08B 3/08; B08B 3/10; B08B 3/102; B08B 3/12; B08B 5/00
USPC ......... 134/56 R, 95.2, 99.1, 102.2, 105, 109, 134/184, 198
See application file for complete search history.

(56) References Cited

FOREIGN PATENT DOCUMENTS

| | | |
|---|---|---|
| JP | 2008-226900 A | 9/2008 |
| JP | 2011-210764 A | 10/2011 |
| JP | 2012-011286 A | 1/2012 |
| JP | 2012-230253 A | 11/2012 |
| WO | 2013/137013 A1 | 9/2013 |

CLEANING DEVICE

TECHNICAL FIELD

The present invention relates to a cleaning device for removing dirt sticking to an object such as a component and a medical instrument which form a pharmaceutical manufacturing machine.

BACKGROUND ART

In the related art, a pharmaceutical tablet is compression-molded by adding a lubricant, or the like to granulated pharmaceuticals, or a material which is obtained by adding and evenly mixing an excipient, a binder, a disintegrant, and other materials into the granulated pharmaceuticals. As a compression molding apparatus in the pharmaceutical manufacturing machine, for example, a tablet machine including a rotary board on which a plurality of mortars are disposed at a peripheral edge, and an upper pestle and a lower pestle which are disposed in a vertically slidable manner in the vertical direction with respect to the rotary board, and the like are known. The tablet machine is configured such that a mortar hole, in which a bottom of the mortar hole is formed by the lower pestle, is filled with powder of a pharmaceutical or a food by using a feeder, the powder is compression-molded by the upper pestle and the lower pestle, a molded product such as a tablet is lifted on the rotary board by raising the lower pestle, and the molded product is extracted by using a damper for taking out a compression-molded product to the outside of the rotary board.

In such a tablet machine, when the pestle is repeatedly press-fit into the mortar, residues of the cured granulated pharmaceutical are deposited on the components of the tablet machine such as an inner peripheral wall of the mortar or an outer peripheral surface and a pressing surface portion of the pestle, and an inner portion of the rotary board. Deposits which are formed of the residues of the pharmaceutical causes damage to an apparatus and a quality defect of the manufactured pharmaceutical, and thus are required to be removed. In addition, similarly in a component of a grinder which is used to improve elution of a poorly water soluble drug in the manufacturing of the pharmaceutical, there is a problem that the residues of the pharmaceutical are deposited, and thus the deposited residues are required to be removed.

In other to remove the residues of the pharmaceutical which are stuck to the component constituting the pharmaceutical manufacturing machine such as the tablet machine and the grinder, the component is cleaned with hands by using a brush; however, such a cleaning operation is complicated and troublesome.

As means for solving the above-described problems, for example, PTL 1 discloses a cleaning device which automatically cleans an object by ejecting high-pressure water. In addition, PTL 2 discloses a cleaning device which cleans the object with a treatment solution prepared by dissolving carbon dioxide although the cleaning device is not for removing the residues of the pharmaceutical which are stuck to the component constituting the pharmaceutical manufacturing machine.

Further, when a body fluid such as blood during the surgery is stuck to a medical instrument used in surgery, if the medical instrument is a radio knife or the like of which the temperature becomes high, the body fluid which is stuck to the medical instrument is burned and fixed due to the heat of the medical instrument. In addition, even in a case of a high reactive chemical, for example, even when the body fluid comes in contact with acid, the body fluid is adversely changed, and fixed to the medical instrument.

In this way, it is not possible to remove the body fluid which is fixed to the medical instrument with a washer disinfector using a general cleaning agent. The cleaning guidelines 2010 by Japanese Society of Medical Instrumentation states "the body fluid which is burned at a tip end of bipolar coagulation forceps cannot be removed by automatic cleaning", and in the actual medical field, for example, the medical instrument with stain is immersed into an alkali cleaning agent for a while, and then is cleaned with hands by using a brush; however, there is a problem in that such a cleaning operation is complicated and troublesome.

As means for solving the above-described problem, for example, PTL 3 discloses a cleaning device which is not for a medical instrument, but for automatically removing a part of work piece which is burned and stuck to a wire net at the time of food processing.

CITATION LIST

Patent Literature

PTL 1: Japanese Unexamined Patent Application Publication No. 2012-11286
PTL 2: Japanese Unexamined Patent Application Publication No. 2011-210764
PTL 3: Japanese Unexamined Patent Application Publication No. 5-192064

SUMMARY OF INVENTION

Technical Problem

However, the cleaning devices which are disclosed in PTL 1 and PTL 2 do not have sufficient cleaning capability for removing the residues of the pharmaceutical which are stuck to the component (the object) constituting the pharmaceutical manufacturing machine. In order to make up for the insufficient cleaning capability, it is considered to use a cleaning fluid which is obtained by mixing with chemicals. However, from the viewpoint of validation, there is concern about using such chemicals. Meanwhile, the validation is one of requirements based on standards on production management and quality control (Good Manufacturing Practice: GMP) of pharmaceuticals or medical tools, foods, and the like, and standards on the implementation of safety testing of pharmaceuticals (Good Laboratory Practice: GLP).

In addition, in order to remove residues of the pharmaceutical which are stuck to a side surface portion of the component (the object) constituting the pharmaceutical manufacturing machine, the cleaning device disclosed in PTL 1 ejects the high-pressure water in the air, and causes a jet flow to occur while involving the air into the cleaning fluid in an immersed state, and thus performs cleaning by indirect physical force. For this reason, the cleaning capability of the cleaning device disclosed in PTL 1 is not sufficient with respect to the side surface portion of the object. In addition, as described above, the cleaning is performed in both a portion that the high-pressure water directly hits, and a portion that the high-pressure water indirectly hits, and thus there is a concern about cleaning unevenness.

In addition, in order to remove the burned part of the work piece, the cleaning device disclosed in PTL 3 ejects the cleaning fluid in the air, and performs cleaning by shower cleaning. For this reason, the cleaning capability of the cleaning device disclosed in PTL 3 is also not sufficient with respect to the medical instrument to which the burned body fluid is fixed.

The present invention is made to solve the above-described problem, and the object thereof is to provide a cleaning device which has high cleaning capability, and can efficiently remove dirt sticking to an object such as a component and a medical instrument which constitute a pharmaceutical manufacturing machine without cleaning unevenness.

Solution to Problem

According to an aspect of the invention, there is provided a cleaning device including: a cleaning fluid retention portion which retains a cleaning fluid for cleaning an object;
a cleaning tank which is capable of accommodating the cleaning fluid;
a cleaning portion which ejects the cleaning fluid, in the cleaning tank; and
a cleaning fluid discharge portion which is connected to the cleaning fluid retention portion, and discharges the cleaning fluid retained in the cleaning fluid retention portion to the cleaning portion in a pressured state,
wherein the cleaning portion includes
a first flow passage which is connected to the cleaning fluid discharge portion, and to which the cleaning fluid which is pressure-fed by the cleaning fluid discharge portion is supplied;
a second flow passage which is continued to a downstream end of the first flow passage, and of which a flow passage cross-sectional area is smaller than that of the first flow passage;
a third flow passage which is continued to a downstream end of the second flow passage, and of which the flow passage cross-sectional area becomes gradually larger as being separated from the second flow passage; and
an accommodating space which is continued to the downstream end of the third flow passage, is capable of accommodating the object, and is opened to the outside.

In addition, in the invention, it is preferable that a size of the accommodating space is sufficient for accommodating the entirety of the object.

Further, in the invention, it is preferable that the first flow passage is formed into a right cylinder shape,
the second flow passage is formed into a right cylinder shape having an outer diameter which is smaller than an outer diameter of the first flow passage, and
the third flow passage is formed into a truncated cone shape having an outer diameter at an upstream end thereof which is equivalent to the outer diameter of the second flow passage, and an outer diameter at a downstream end thereof which is larger than the outer diameter of the second flow passage.

In addition, in the invention, it is preferable that the accommodating space is formed into a right cylinder shape having an outer diameter which is the same or substantially the same as the outer diameter of the third flow passage at the downstream end.

Further, in the invention, it is preferable that the cleaning portion is provided with a projecting portion which is projected inwardly in an inner periphery portion which forms the accommodating space.

In addition, in the invention, it is preferable that the flow passage cross-sectional area of the second flow passage is determined such that the cleaning fluid which flows the third flow passage becomes a cleaning fluid containing minute bubbles caused by cavitation.

According to another aspect of the invention, there is provided a cleaning device including: a cleaning tank which is capable of accommodating an object;
a cleaning fluid retention portion which retains a cleaning fluid for cleaning the object;
a cleaning fluid discharge portion which is connected to the cleaning fluid retention portion, and pressure-feeds the cleaning fluid retained in the cleaning fluid retention portion in a pressured state;
a gas retention portion which retains a gas fluid in a pressured state, and is capable of pressure-feeding the gas fluid; and
a fluid ejecting nozzle which is provided in the cleaning tank,
wherein the fluid ejecting nozzle includes a gas feed portion which is connected to the gas retention portion via a gas-passing pipe, and includes a gas feed flow passage to which the gas fluid which is pressure-fed from the gas retention portion is supplied;
a cleaning fluid feed portion which is connected to the cleaning fluid discharge portion via a cleaning fluid-passing pipe, and includes a cleaning fluid feed flow passage to which the cleaning fluid which is pressure-fed by the cleaning fluid discharge portion;
a gas-liquid mixture portion which is connected to the gas feed portion and the cleaning fluid feed portion, and includes a gas-liquid mixture flow passage in which the gas fluid which is pressure-fed from the gas feed flow passage and the cleaning fluid which is pressure-fed from the cleaning fluid feed flow passage are mixed with each other; and
an ejecting portion which is connected to the gas-liquid mixture portion, includes a mixed fluid-passing flow passage in which the gas-liquid mixture fluid mixed in the gas-liquid mixture flow passage flows, and ejects the gas-liquid mixture fluid from the mixed fluid-passing flow passage.

In addition, in the invention, it is preferable that a flow rate of the gas-liquid mixture fluid which is ejected from the ejecting portion is equal to or greater than 20 L/min.

Further, in the invention, it is preferable that the gas fluid is carbon dioxide.

Further, in the invention, it is preferable that the flow passage cross-sectional area of the gas-liquid mixture flow passage is smaller than the flow passage cross-sectional areas of the cleaning fluid feed flow passage and the mixed fluid-passing flow passage.

Further, in the invention, it is preferable that the flow passage cross-sectional area of the gas-liquid mixture flow passage is set such that the gas-liquid mixture fluid flowing into the mixed fluid-passing flow passage becomes a fluid containing minute bubbles caused by cavitation.

Advantageous Effects of Invention

According to the invention, the cleaning device is provided with the cleaning tank, the cleaning fluid retention portion which retains the cleaning fluid for cleaning the object, the cleaning fluid discharge portion which is connected to the cleaning fluid retention portion, and discharges the cleaning fluid retained in the cleaning fluid retention portion in a pressured state, and a pipe of which one end portion is connected to the cleaning fluid discharge portion, and the cleaning portion which ejects the cleaning fluid, in the cleaning tank. The cleaning portion may be installed so as to be immersed in the cleaning fluid. The cleaning portion includes a first flow passage which is connected to the other end portion of the pipe, and to which the cleaning fluid which is pressure-fed by the cleaning fluid discharge portion is supplied, a second flow passage which is continued to a downstream end of the first flow passage, and of which a flow passage cross-sectional area is smaller than that of the first flow passage, a third flow passage which is continued to a downstream end of the second flow passage, and of which a flow passage cross-sectional area becomes gradually larger as being separated from the second flow passage, and an accommodating space which is continued to a downstream end of the third flow passage, and is capable of accommodating the object.

In the cleaning device configured as described above, when the object is disposed in the accommodating space, and the cleaning fluid which is in a pressured state is supplied from the cleaning fluid discharge portion to the first flow passage in the cleaning portion, the cleaning fluid flowing through the second flow passage is ejected to the accommodating space via the third flow passage. With this, it is possible to efficiently impart the jet flow caused by the cleaning fluid to the outer surface of the object which is disposed in the accommodating space, thereby realizing high cleaning capability. Therefore, even though the object is a component having a pillar or bar-like structure, among components constituting a pharmaceutical manufacturing machine, or a medical instrument having a pillar or bar-like structure, such as a pestle of a tablet machine, an endoscopic surgical instrument, and a radio knife, it is possible to efficiently remove dirt such as residues of a pharmaceutical and an adversely changed body fluid which are stuck to the object.

In addition, according to the invention, the size of the accommodating space is sufficient for accommodating the entirety of the object. Therefore, among the components constituting the pharmaceutical manufacturing machine, in the component having the pillar or bar-like structure or the medical instrument having the pillar or bar-like structure, it is possible to efficiently impart the jet flow caused by the cleaning fluid to not only the tip end portion on one side in the longitudinal direction but also the side surface portion thereof, thereby cleaning the entirety of the object with strong physical force. Accordingly, it is possible to efficiently remove the residues of the pharmaceutical, the oil stain, the blood stain, and the like which are stuck to the side surface portion without cleaning unevenness.

In addition, according to the invention, the first flow passage is formed into a right cylinder shape, the second flow passage is formed into a right cylinder shape having the outer diameter which is smaller than the outer diameter of the first flow passage, and the third flow passage is formed into a truncated cone shape having the outer diameter at the upstream end thereof which is equivalent to the outer diameter of the second flow passage, and the outer diameter at the downstream end which is larger than the outer diameter of the second flow passage. That is, the cleaning portion has a so-called venturi tube structure. With such a venturi tube structure, some of the pressure energy of the fluid is replaced with speed energy, and it is possible to eject the cleaning fluid having the flow rate accelerated in the second flow passage of which the flow passage cross-sectional area is reduced, to the accommodating space via the third flow passage. As a result, as described above, even though the object is, among components constituting a pharmaceutical manufacturing machine, a component having a pillar or bar-like structure or a medical instrument having a pillar or bar-like structure, it is possible to efficiently remove dirt such as the residues of the pharmaceutical and the adversely changed body fluid which are stuck to the object.

Further, according to the invention, the accommodating space is formed into a right cylinder shape having an outer diameter which is the same or substantially the same as the outer diameter of the third flow passage at the downstream end. With this, in the ejecting hole which is formed in the third flow passage, it is possible to guide the physical force which works in a bus line direction into the accommodating space without the force being lost in the cleaning tank. As a result, as described above, even though the object is, among components constituting a pharmaceutical manufacturing machine, a component having a pillar or bar-like structure or a medical instrument having a pillar or bar-like structure, it is possible to efficiently remove dirt such as the residues of the pharmaceutical and the adversely changed body fluid which are stuck to the object.

Further, according to the invention, the cleaning portion is provided with a projecting portion which is projected inwardly in an inner periphery portion which forms the accommodating space. With this, it is possible to guide the physical force which works in the direction parallel with the side surface of the object which is guided in the accommodating space to the direction perpendicular to the side surface of the object by the projecting portion. As a result, as described above, even though the object is, among components constituting a pharmaceutical manufacturing machine, a component having a pillar or bar-like structure or a medical instrument having a pillar or bar-like structure, it is possible to efficiently remove dirt such as residues of the pharmaceutical, the oil stain, the grease stain, and an adversely changed body fluid which are particularly stuck to the side surface of the object.

Further, according to the invention, the flow passage cross-sectional area of the second flow passage is determined such that the cleaning fluid which flows in the third flow passage becomes a cleaning fluid containing minute bubbles caused by the cavitation. In this way, when the object is cleaned by the gas-liquid mixture fluid containing the bubbles caused by the cavitation, the impact generated when the bubbles are collapsed can be imparted to the object for cleaning, and thus it is possible to efficiently remove the dirt such as the residues of the pharmaceutical and the adversely changed body fluid which are stuck to the object.

According to the invention, the cleaning device is provided with the cleaning tank which is capable of accommodating the object, the cleaning fluid retention portion which retains the cleaning fluid, the cleaning fluid discharge portion which pressure-feeds the cleaning fluid retained in the cleaning fluid retention portion in a pressured state, the gas retention portion which retains the gas fluid in a pressured state, and is capable of pressure-feeding the gas fluid, and the fluid ejecting nozzle. The fluid ejecting nozzle includes the gas feed portion, the cleaning fluid feed portion, the gas-liquid mixture portion, and the ejecting portion. The gas feed portion of the ejecting nozzle includes a gas feed flow passage to which the gas fluid which is pressure-fed from the gas retention portion is supplied. The cleaning fluid feed portion includes a cleaning fluid feed flow passage to which the cleaning fluid which is discharged from the cleaning fluid retention portion by the cleaning fluid discharge portion is supplied. The gas-liquid mixture portion is connected to the gas feed portion and the cleaning fluid feed portion, and includes a gas-liquid mixture flow passage in which the gas fluid which is pressure-fed from the gas feed flow passage and the cleaning fluid which is pressure-fed from the cleaning fluid feed flow passage are mixed with each other. The ejecting portion is connected to the gas-liquid mixture portion, includes a mixed fluid-passing flow passage in which the gas-liquid mixture fluid mixed in the gas-liquid mixture flow passage flows, and ejects the gas-liquid mixture fluid from the mixed fluid-passing flow passage in the cleaning tank.

In the cleaning device configured as described above, in the fluid ejecting nozzle which is provided in the cleaning tank, the gas fluid, which is pressure-fed from the gas retention portion and supplied into the gas feed flow passage of the gas feed portion, and the cleaning fluid, which is pressure-fed from the cleaning fluid retention portion by the cleaning fluid discharge portion and supplied into the cleaning fluid feed flow passage of the cleaning fluid feed portion, are mixed in the gas-liquid mixture flow passage of the gas-liquid mixture portion, and the mixed gas-liquid mixture fluid flows into the mixed fluid-passing flow passage of the ejecting portion and is ejected into the cleaning tank from the mixed fluid-passing flow passage. In this way, the cleaning device of the invention, as the gas-liquid mixture fluid which is obtained by mixing the cleaning fluid and the gas fluid is ejected from the fluid ejecting nozzle so as to clean the object, has high cleaning capability, thereby efficiently removing residues of the pharmaceutical which are stuck to the component (the object) constituting the pharmaceutical manufacturing machine.

In addition, according to the invention, the flow rate of the gas-liquid mixture fluid which is ejected from the ejecting portion in the fluid ejecting nozzle is equal to or greater than 20 L/min. With this, since it is possible to eject the high flow rate of the gas-liquid mixture fluid to the object, the object can be cleaned by the strong physical force, and thus it is possible to efficiently remove the residues of the pharmaceutical which are stuck to the component (the object) constituting the pharmaceutical manufacturing machine.

Further, according to the invention, as the gas fluid which is pressure-fed from the gas retention portion, the carbon dioxide is used. With this, in addition to the physical force which is caused by ejection of the gas-liquid mixture fluid, it is possible to clean the object by using the chemical force of the carbon dioxide, and thus it is possible to efficiently remove the residues of the pharmaceutical which are stuck to the component (the object) constituting the pharmaceutical manufacturing machine.

In addition, according to the invention, in the fluid ejecting nozzle, the flow passage cross-sectional area of the gas-liquid mixture flow passage of the gas-liquid mixture portion is smaller than the flow passage cross-sectional area of the cleaning fluid feed flow passage of the cleaning fluid feed portion, and the flow passage cross-sectional area of the mixed fluid-passing flow passage of the ejecting portion. Such a fluid ejecting nozzle has a so-called venturi tube structure in that the flow passage cross-sectional area of the gas-liquid mixture portion which is positioned between the cleaning fluid feed portion corresponding to an inlet to which the cleaning fluid is supplied, and the ejecting portion corresponding to an outlet from which the gas-liquid mixture fluid is ejected is reduced. In the fluid ejecting nozzle having such a venturi tube structure, some of the pressure energy of the fluid is replaced with the speed energy, and thus it is possible to eject the gas-liquid mixture fluid having the flow rate accelerated in the gas-liquid mixture portion of which the flow passage cross-sectional area is reduced from the ejecting portion. As a result, it is possible to efficiently remove the residues of the pharmaceutical which are stuck to the component (the object) constituting the pharmaceutical manufacturing machine.

Further, according to the invention, in the fluid ejecting nozzle, the flow passage cross-sectional area of the gas-liquid mixture flow passage of the gas-liquid mixture portion is set such that the gas-liquid mixture fluid flowing into the mixed fluid-passing flow passage of the ejecting portion becomes a fluid containing minute bubbles caused by cavitation. In this way, when the object is cleaned by the gas-liquid mixture fluid containing the bubbles caused by the cavitation, the impact generated when the bubbles are collapsed can be imparted to the object for cleaning, and thus it is possible to efficiently remove residues of the pharmaceutical which are stuck to the component (the object) constituting the pharmaceutical manufacturing machine.

BRIEF DESCRIPTION OF DRAWINGS

An object, features, and advantages of the present invention will be more apparent from the detailed description and drawings below.

DESCRIPTION OF EMBODIMENTS

First Embodiment

Figure 1:
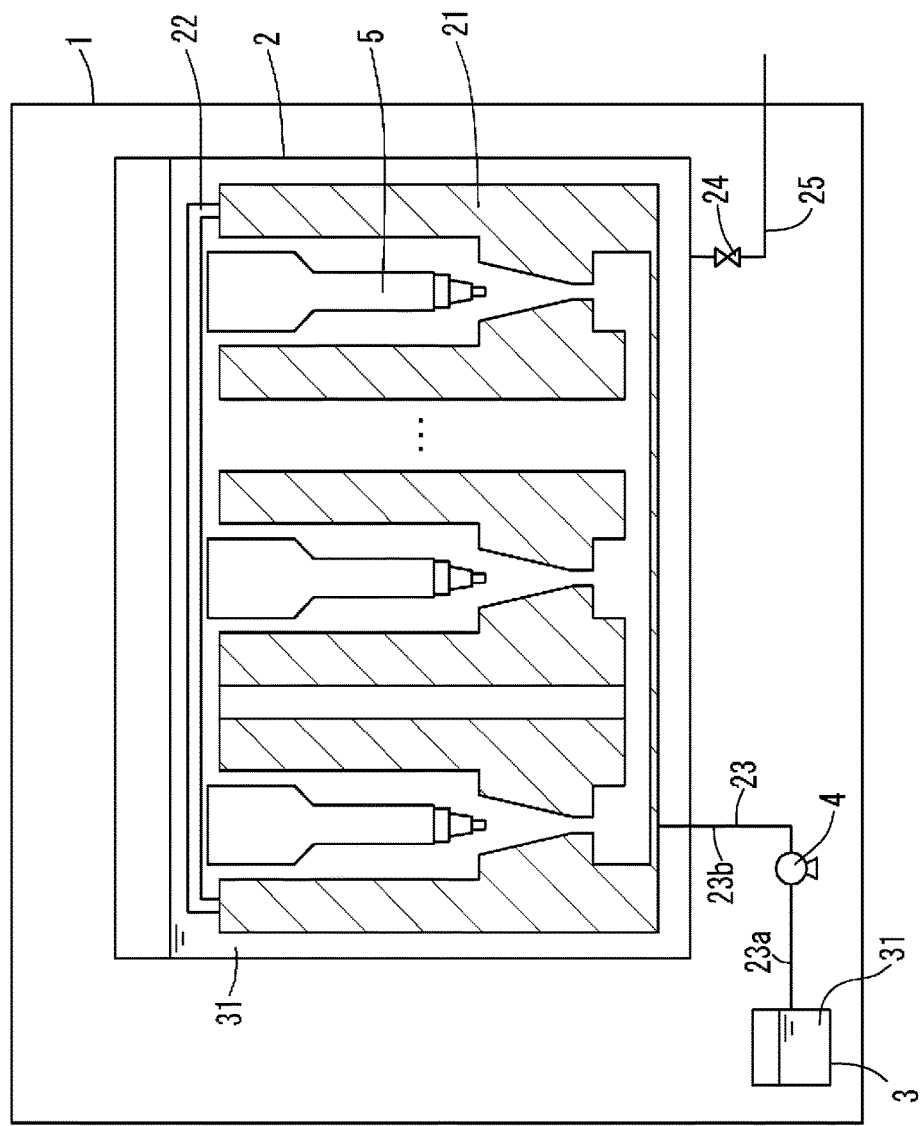
FIG. 1 is a diagram schematically illustrating a configuration of a cleaning device 100 according to a first embodiment of the invention.

FIG. 1 is a diagram schematically illustrating a configuration of a cleaning device 100 according to a first embodiment of the invention. It is possible to realize a cleaning method of the invention by using the cleaning device 100.

The cleaning device 100 is an apparatus which cleans an object 5 such as a component for constituting a pharmaceutical manufacturing machine and a medical instrument, and an apparatus for removing dirt such as residues of a pharmaceutical (powder), oil, and grease which are stuck to the component for constituting the pharmaceutical manufacturing machine, and a body fluid which is burned and stuck to the medical instrument by a physical force and a chemical force.

Examples of the object 5 such as a component constituting a pharmaceutical manufacturing machine which performs a cleaning treatment in the cleaning device 100 include a mortar, a pestle, and a rotary board of a tablet machine which compression-molds a tablet for a pharmaceutical, and a rotary board of a grinder. The residues of a cured granulated pharmaceutical, oil, grease, and the like are stuck to the mortar, the pestle, and the rotary board.

In addition, examples of the object 5 such as a medical instrument which performs the cleaning treatment in the cleaning device 100 include an endoscopic surgical instrument, a radio knife, and the like. The body fluid which is burned by heat and adversely changed by chemicals (hereinafter, referred to as "burned component") and the like are stuck to the endoscopic surgical instrument, the radio knife, and the like.

The cleaning device 100 in the embodiment is configured so as to remove the object 5 of the component of the pharmaceutical manufacturing machine to which the aforementioned dirt of the pharmaceutical and the oil stain are stuck, or the object 5 of the medical instrument to which the aforementioned burned component is fixed by using a jet flow occurring in a cleaning nozzle member 21 which serves as a fluid ejecting nozzle in a cleaning tank 2. Particularly, the cleaning device 100 is preferably used to a component or a medical instrument which have a pillar or bar-like structure. The object 5 may be immersed in a cleaning fluid 31 at the time of cleaning.

The cleaning device 100 is provided with a case 1 which becomes an outline. In the case 1, the cleaning tank 2, a retention tank 3, a liquid feeding pump 4, and a cleaning fluid feed pipe 23 are retained. In the cleaning device 100 in the embodiment, a cleaning fluid retention portion is formed of the retention tank 3, and a cleaning fluid discharge portion is formed of the liquid feeding pump 4 and the cleaning fluid feed pipe 23.

In the cleaning tank 2, a plurality of cleaning nozzle members 21 which are formed to impart the jet flow with respect to the object 5 are installed, and, a fixing jig 22 which supports the object 5 in a state of being disposed in a guide pipe flow passage S4 described below is provided. The plurality of cleaning nozzle members 21 are integrally provided such that large-diameter flow passages S1 described below communicate with each other. The cleaning nozzle member 21 may be fixed to the inside of the cleaning tank 2, or may be movably formed with respect to the object 5 which is supported by the fixing jig 22, by separately providing a driving mechanism. Alternatively, the driving mechanism may be provided so as to move the object 5 with respect to the cleaning nozzle member 21.

The cleaning tank 2 and the retention tank 3 are connected to each other via the cleaning fluid feed pipe 23. The liquid feeding pump 4 is connected to the cleaning fluid feed pipe 23. Specifically, the cleaning fluid feed pipe 23 includes a first pipe 23a and a second pipe 23b, and the liquid feeding pump 4 is connected to the retention tank 3 via the first pipe 23a. In addition, one end portion of the second pipe 23b is connected to the liquid feeding pump 4, and the other end portion thereof is connected to the cleaning nozzle member 21.

The cleaning fluid 31 which is retained in the retention tank 3 is pressure-fed by driving the liquid feeding pump 4 in a state where the inside of the second pipe 23b is pressured, and supplied to the large-diameter flow passage S1 described below in the cleaning nozzle member 21. In addition, although not shown, a configuration such that liquid feeding ports of the cleaning tank 2 and the liquid feeding pump 4 are connected to each other by using a pipe, and the cleaning fluid 31 is circulated via the liquid feeding pump 4 may be employed. In this way, the cleaning fluid 31, in a state of being pressured, which is supplied from the liquid feeding pump 4 to the cleaning nozzle member 21 is ejected in the cleaning nozzle member 21 so as to cause a jet flow to occur, and then retained in the cleaning tank 2.

As the cleaning fluid 31, in a case of cleaning the component of the pharmaceutical manufacturing machine, for example, pure water is desirable; however, ozone water or an organic acid such as an oxalic acid, a citric acid, a formic acid, a lactic acid, glycolic acid, or acetic acid, alkali ion water, a neutral cleaning agent, and the like may be used. The cleaning fluid 31 does not remain in the pharmaceutical manufacturing machine after being used, and is excellent in safety, and thus is desirable from the viewpoint of validation. Particularly, when removing stains on metal such as insoluble calcium salt or magnesium salt, and an iron oxide, it is preferable to use an organic acid.

In addition, as the cleaning fluid 31, when cleaning the medical instrument, it is preferable to use a compound having a capability of decomposing a burned protein component. Examples of such a compound include a surfactant, a sodium hydroxide, a neutral enzymatic cleaning agent, a perchloric acid (a bleaching agent), a bleach activator, a chelating agent, and a silver compound. In addition, in this case, it is preferable that the concentration of the cleaning fluid 31 is set to be in a range of 0.5 wt % to 4 wt %. Further, it is preferable that the cleaning fluid 31 has a pH of 6.0 to 11.0.

In addition, a drain pipe 25 is connected to a bottom of the cleaning tank 2, and a drain valve 24 which can open and close a flow passage formed in the drain pipe 25 is connected to the drain pipe 25. With this, after completing the cleaning treatment in the cleaning device 100, the used cleaning fluid 31 which is retained in the cleaning tank 2 can be discharged to the outside of the cleaning tank 2. Specifically, it is possible to discharge the used cleaning fluid 31 through the drain pipe 25 by switching the drain valve 24 from a close state into an open state.

Figure 2:
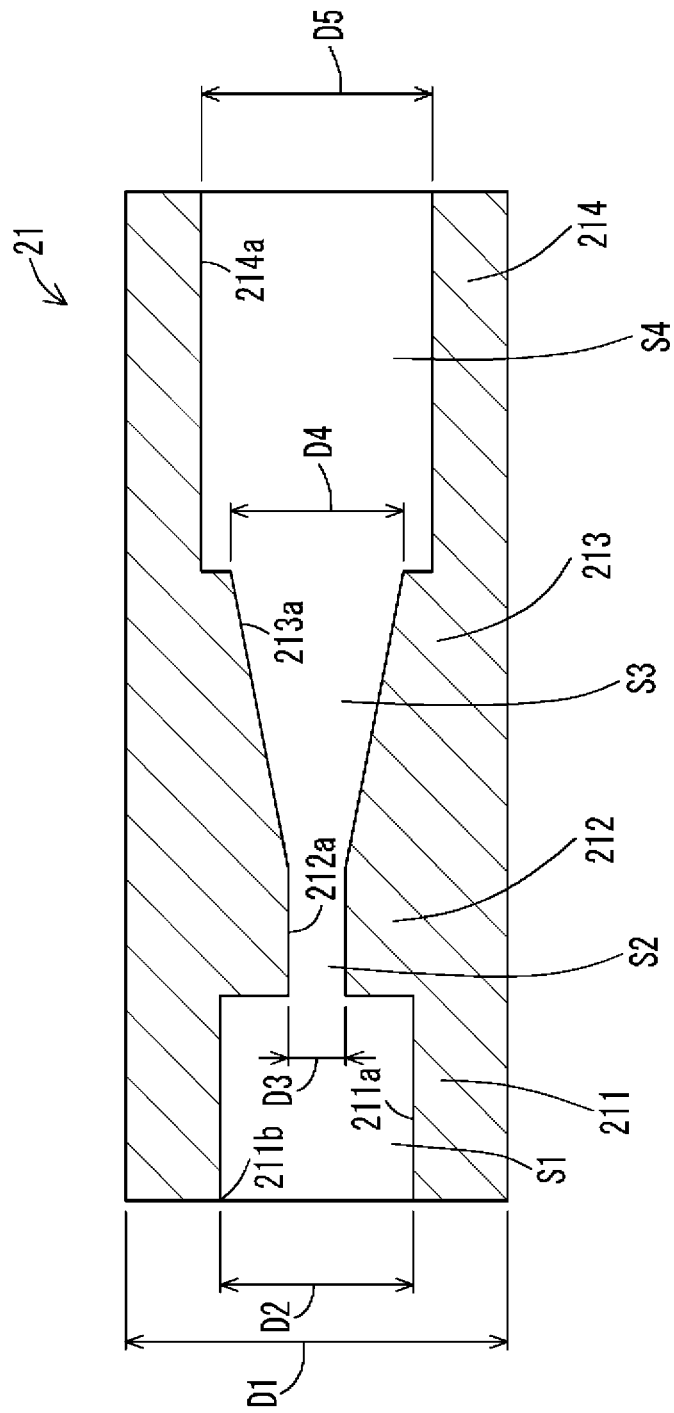
FIG. 2 is an enlarged diagram illustrating a configuration of a cleaning nozzle member 21.

FIG. 2 is an enlarged diagram illustrating a configuration of a cleaning nozzle member 21. The cleaning nozzle member 21 is installed in the cleaning tank 2, and is connected to the retention tank 3 in which the cleaning fluid 31 is retained via the cleaning fluid feed pipe 23. The cleaning nozzle member 21 may be installed so as to be immersed in the cleaning fluid 31. The cleaning nozzle member 21 is formed so as to eject the cleaning fluid 31 which is supplied via the cleaning fluid feed pipe 23 in the inside thereof, and specifically, the cleaning nozzle member 21 is formed of a large pipe diameter part 211, a small pipe diameter part 212, a conical pipe diameter part 213, and a guide pipe diameter portion 214. In the embodiment, the cleaning nozzle member 21 is formed so as to include a right cylindrical outer peripheral surface.

The large-diameter flow passage S1 (a first flow passage) to which the cleaning fluid 31 which is pressure-fed by a liquid feeding pump 4 is supplied from a retention tank 3 is formed in the large pipe diameter part 211, and the cleaning fluid feed port 211b to which the cleaning fluid 31 which is pressure-fed by the liquid feeding pump 4 is supplied is provided at an upstream end of the large-diameter flow passage S1. That is, the cleaning fluid 31 which is pressure-fed by the liquid feeding pump 4 flows into the large-diameter flow passage S1 via a cleaning fluid feed port 211b.

In the embodiment, the large-diameter flow passage S1 having a right cylinder shape is formed of a right cylindrical inner periphery surface 211a which is formed in the large pipe diameter part 211. An outer diameter D1 of the cleaning nozzle member 21 is, for example, 40.0 mm, and an outer diameter D2 of the large-diameter flow passage S1 (that is, an inner diameter of the inner periphery surface 211a) is, for example, 20.0 mm.

The small pipe diameter part 212 is integrally formed by being continued to the large pipe diameter part 211. A small-diameter flow passage S2 (a second flow passage), which is continued to a downstream end of the large-diameter flow passage S1 of the large pipe diameter part 211 and includes a flow passage cross-sectional area which is smaller than that of the large-diameter flow passage S1, is formed in the small pipe diameter part 212. That is, the cleaning fluid 31 which is supplied to the large-diameter flow passage S1 flows into the small-diameter flow passage S2 via the downstream end of the large-diameter flow passage S1. Since the small-diameter flow passage S2 includes the flow passage cross-sectional area which is smaller than the flow passage cross-sectional area of the large-diameter flow passage S1, the cleaning fluid 31 which flows into the small-diameter flow passage S2 flows down the small-diameter flow passage S2 at a speed faster than the speed at the time of flowing down the large-diameter flow passage S1. That is, the flowing speed of the cleaning fluid 31 which is supplied to the large-diameter flow passage S1 becomes faster in the small-diameter flow passage S2.

In the embodiment, the small-diameter flow passage S2 having a right cylinder shape is formed of a right cylindrical inner periphery surface 212a which is formed in the small pipe diameter part 212, and is provided with the same axis as that of the large-diameter flow passage S1. The outer diameter D3 (that is, the inner diameter of the inner periphery surface 212a) of the small-diameter flow passage S2 is smaller than the outer diameter D2 of the large-diameter flow passage S1, and for example, is 6.0 mm. Therefore, a step is formed between the large-diameter flow passage S1 and the small-diameter flow passage S2.

The conical pipe diameter part 213 is integrally formed by being continued to the small pipe diameter part 212. A conical flow passage S3 (a third flow passage) which is continued to a downstream end of the small-diameter flow passage S2 of the small pipe diameter part 212 is formed in the conical pipe diameter part 213 such that the flow passage cross-sectional area thereof becomes gradually larger as being separated from the small-diameter flow passage S2. That is, the cleaning fluid 31 which is supplied to the small-diameter flow passage S2 flows into the conical flow passage S3 via the downstream end of the small-diameter flow passage S2. Since the flow passage cross-sectional area of the conical flow passage S3 becomes gradually larger as being separated from the small-diameter flow passage S2 as described above, the cleaning fluid 31 of which the speed becomes faster in the small-diameter flow passage S2 is ejected to a guide pipe flow passage S4 described below via the conical flow passage S3, and thereby the jet flow occurs.

In the embodiment, the conical flow passage S3 having a truncated cone shape is formed of a cylindrical inner periphery surface 213a of which the cross-section is formed into a circular shape and the inner diameter becomes gradually larger, and is provided with the same axis as that of the small-diameter flow passage S2. The outer diameter of the conical flow passage S3 at the upstream end is equivalent to the outer diameter D3 of the small-diameter flow passage S2, and the outer diameter D4 of the conical flow passage S3 at the downstream end is larger than the outer diameter D3 of the small-diameter flow passage S2, and for example, is 15.0 mm. Accordingly, the small-diameter flow passage S2 and the conical flow passage S3 communicate with each other without a step.

A guide pipe diameter part 214 is integrally formed by being continued to the conical pipe diameter part 213. A guide pipe flow passage S4 (an accommodating space) which is continued to the downstream end of the conical flow passage S3 of the conical pipe diameter part 213, is capable of accommodating the entirety of the object 5, and is open to the outside is formed in the guide pipe diameter part 214. That is, the cleaning fluid 31 which is supplied to the conical flow passage S3 flows into the guide pipe flow passage S4 via the downstream end of the conical flow passage S3. In addition, the cleaning fluid 31 which flows into the guide pipe flow passage S4 is discharged into the cleaning tank 2 via an opening of the downstream end of the guide pipe flow passage S4 after being used for cleaning the object 5. Further, the object 5 is disposed in the guide pipe flow passage S4 via an opening of the downstream end of the guide pipe flow passage S4. Particularly, the pillar or bar-like object 5 is disposed in the guide pipe flow passage S4 in a state where the longitudinal direction thereof and the axial direction of the guide pipe flow passage S4 are matched with each other.

In the embodiment, the guide pipe flow passage S4 having the right cylinder shape is formed of a right cylindrical inner periphery surface 214a which is formed in the guide pipe diameter part 214 and is provided with the same axis as that of the conical flow passage S3. An outer diameter (that is, the inner diameter of the inner periphery surface 214a) D5 of the guide pipe flow passage S4 is larger than the outer diameter D4 of the conical flow passage S3 at the downstream end and, for example, is 32.0 mm. Accordingly, a step is formed between the conical flow passage S3 and the guide pipe flow passage S4.

Note that, regarding the outer diameter D5 of the guide pipe flow passage S4, when the pillar or bar-like object 5 is disposed in the guide pipe flow passage S4 by matching the longitudinal direction thereof with the axial direction of the guide pipe flow passage S4, a clearance between the inner periphery surface 214a of the guide pipe diameter part 214 and the outer surface of the object 5 is preferably about 2.0 mm to 10.0 mm. With such a clearance in a numerical range, it is possible to guide the jet flow into the guide pipe diameter part 214 without losing a physical force, which is caused by the jet flow of the cleaning fluid 31 which is ejected to the guide pipe flow passage S4 via the conical flow passage S3, working in a bus line direction in the cleaning tank 2. With this, it is possible to impart a strong physical force to the side surface portion of the object 5 as well.

In the cleaning nozzle member 21, the large pipe diameter part 211, the small pipe diameter part 212, the conical pipe diameter part 213, and the guide pipe diameter part 214 are integrally formed by being continued in this order, and each axial line of the large-diameter flow passage S1, the small-diameter flow passage S2, the conical flow passage S3, and the guide pipe flow passage S4 is provided on the same axial line.

In the cleaning device 100 formed as described above, in the cleaning nozzle member 21, the flow passage cross-sectional area of the small-diameter flow passage S2 which is positioned between the large-diameter flow passage S1 corresponding to an inlet to which the cleaning fluid 31 is supplied, and the conical flow passage S3 corresponding to an outlet from which the cleaning fluid 31 is discharged is reduced to be smaller than the flow passage cross-sectional area of each of the large-diameter flow passage S1 and the conical flow passage S3, and with this, the cleaning nozzle member 21 has a so-called venturi tube structure.

In the cleaning nozzle member 21 having such a venturi tube structure, some of the pressure energy of the fluid is replaced with a speed energy, and thus it is possible to eject the cleaning fluid 31 having the flow rate accelerated in the small-diameter flow passage S2 of which the flow passage cross-sectional area is reduced, to the guide pipe flow passage S4 via the conical flow passage S3. As a result, with the jet flow of the cleaning fluid 31, it is possible to efficiently remove the dirt (dirt of the pharmaceutical, oil stain, blood stain, or the like) sticking to the object 5, which is disposed in the guide pipe flow passage S4, such as the component and the medical instrument which constitute the pharmaceutical manufacturing machine.

In addition, in the cleaning nozzle member 21, the flow passage cross-sectional area of the small-diameter flow passage S2 of the small pipe diameter part 212 is set such that the fluid flowing into the conical flow passage S3 of the conical pipe diameter part 213 causes the cavitation. With such a cavitation, the fluid contains minute bubbles. When the object 5 is cleaned by the fluid containing the bubbles caused by the cavitation, the impact generated when the bubbles are collapsed can be imparted to the object 5 for cleaning, and thus it is possible to efficiently remove the dirt (the dirt of the pharmaceutical, the oil stain, the blood stain, or the like) sticking to the object 5 such as the component and the medical instrument which constitute the pharmaceutical manufacturing machine.

Further, in the embodiment, it is preferable that the flow rate of the cleaning fluid 31 which is ejected via the conical flow passage S3 of the conical pipe diameter part 213 in the cleaning nozzle member 21 is equal to or greater than 20 L/min. With this, it is possible to eject the cleaning fluid 31 having a high flow rate to the object 5, and thus the object 5 can be cleaned by the strong physical force, and thereby it is possible to efficiently remove the dirt (the dirt of the pharmaceutical, the oil stain, the blood stain, or the like) sticking to the object 5 such as the component and the medical instrument which constitute the pharmaceutical manufacturing machine.

In addition, it is preferable that the temperature of the cleaning fluid 31 is adjusted by installing heating means such as a heat element at a position on the upstream side further than the conical pipe diameter part 213, for example, in the large-diameter flow passage S1 such that the temperature of the cleaning fluid 31 which is ejected via the conical flow passage S3 of the conical pipe diameter part 213 in the cleaning nozzle member 21 is set to be, for example, 40° C. to 80° C. Alternatively, when the temperature of the cleaning fluid 31 is high due to the pressure by the liquid feeding pump 4, the temperature may be adjusted to be in the aforementioned temperature range by circulating cool water in the outside of the cleaning tank 2. By setting the temperature range, it is possible to further improve the cleaning effect.

In addition, as described above, in the cleaning nozzle member 21, by setting the clearance between the inner periphery surface 214a of the guide pipe diameter part 214 and the outer surface of the object 5 to be about 2.0 mm to 10.0 mm, it is possible to guide the jet flow into the guide pipe diameter part 214 without losing a physical force, which is caused by the jet flow of the cleaning fluid 31 which is ejected to the guide pipe flow passage S4 via the conical flow passage S3, working in a bus line direction in the cleaning tank 2. With this, it is possible to impart a strong physical force to the side surface portion of the object 5 as well, and thus it is possible to efficiently remove the dirt (the dirt of the pharmaceutical, the oil stain, the blood stain, or the like) sticking to the side surface portion of the object 5 such as the component and the medical instrument which constitute the pharmaceutical manufacturing machine, or the dirt (residues of the pharmaceutical, oil, and grease, or the like) sticking to the side surface portion of the object 5 such as the medical instrument.

Second Embodiment

Figure 3:
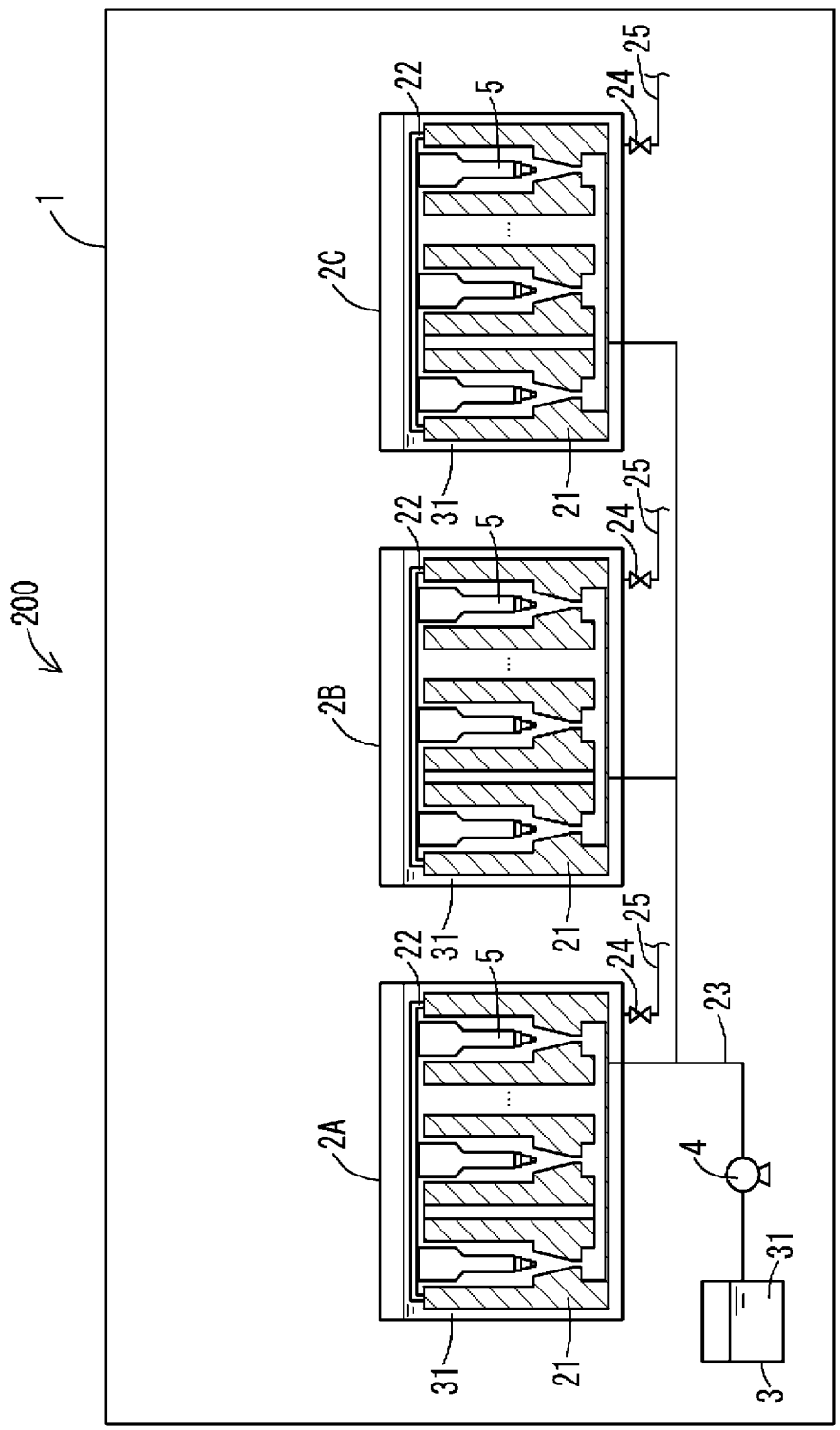
FIG. 3 is a diagram schematically illustrating a configuration of a cleaning device 200 according to a second embodiment of the invention.

FIG. 3 is a diagram schematically illustrating a configuration of a cleaning device 200 according to a second embodiment of the invention. A configuration of the cleaning device 200 is similar to that of the cleaning device 100 in the first embodiment, and thus corresponding constituent elements are given the same reference numerals, and the description thereof will be omitted.

In the cleaning device 200, a plurality of cleaning tanks 2A, 2B, and 2C which are formed in the same way as the cleaning tank 2 provided in the cleaning device 100 as described above are arranged in parallel. Each of the cleaning tanks 2A, 2B, and 2C is provided with a plurality of the cleaning nozzle members 21 similarly in the cleaning tank 2. FIG. 3 illustrates three cleaning tanks 2A, 2B, and 2C which are arranged in parallel, but the number of the cleaning tanks is not limited thereto, for example, two cleaning tanks, or four or more of cleaning tanks may be arranged in parallel.

Each of the cleaning tanks 2A, 2B, and 2C and the retention tank 3 are connected to each other via the cleaning fluid feed pipe 23. The liquid feeding pump 4 is connected to the cleaning fluid feed pipe 23. The cleaning fluid 31 retained in the retention tank 3 is pressure-fed by driving the liquid feeding pump 4 in a state where the inside of the cleaning fluid feed pipe 23 is pressured, and supplied into each of the cleaning tanks 2A, 2B, and 2C. In addition, although not shown, a configuration such that liquid feeding ports in each of the cleaning tanks 2A, 2B, and 2C, and the liquid feeding pump 4 are connected to each other by using a pipe, and the cleaning fluid 31 is circulated via the liquid feeding pump 4 may be employed.

In the cleaning device 200 including the plurality of cleaning tanks 2A, 2B, and 2C which are arranged in parallel, it is possible to perform the cleaning treatment on the object 5 which is disposed in the guide pipe flow passage S4 by the physical force caused by ejecting the cleaning fluid 31 of which the speed becomes faster in the small-diameter flow passage S2 of each of the cleaning nozzle members 21 of each of the cleaning tanks 2A, 2B, and 2C. In such a cleaning device 200, it is possible to prevent the ejecting force of the cleaning fluid 31 from being deteriorated in each of the cleaning nozzle members 21 of each of the cleaning tanks 2A, 2B, and 2C, and to perform the cleaning treatment on a plurality of the objects 5.

Third Embodiment

Figure 4:
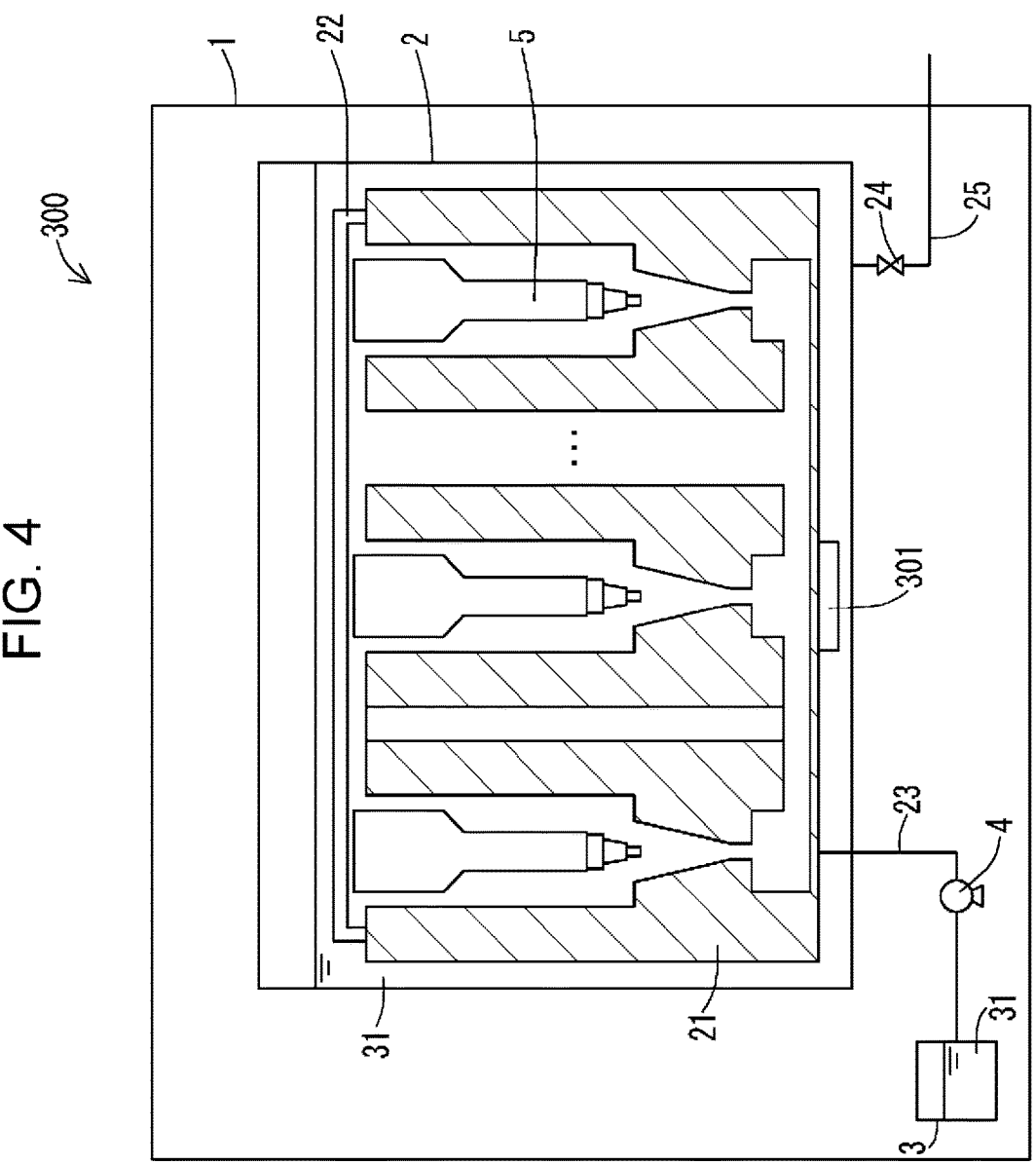
FIG. 4 is a diagram schematically illustrating a configuration of a cleaning device 300 according to a third embodiment of the invention.

FIG. 4 is a diagram schematically illustrating a configuration of a cleaning device 300 according to a third embodiment of the invention. The configuration of the cleaning device 300 is similar to that of the cleaning device 100 in the first embodiment, and thus corresponding constituent elements are given the same reference numerals, and the description thereof will be omitted.

The cleaning device 300 is configured to clean the object 5 by further imparting the ultrasonic vibration as a physical force to the above-described cleaning device 100.

The cleaning device 300 is formed of the cleaning tank 2 which is provided in the cleaning device 100 in the first embodiment, and an ultrasonic wave generating unit 301. The ultrasonic wave generating unit 301 is installed by coming in contact with the cleaning nozzle member 21, and generates ultrasonic waves when the object 5 is cleaned with the jet flow caused by the cleaning fluid 31.

Accordingly, in the cleaning device 300, in addition to the cleaning of the object 5 by ejecting the cleaning fluid 31 of which the speed becomes faster in the small-diameter flow passage S2 of the cleaning device 100 in the first embodiment to the object 5, it is possible to promote peeling off the dirt sticking to the surface of the object 5 by imparting the physical force caused by the ultrasonic vibration to the object 5, and thus it is possible to further improve the cleaning effect.

Herein below, the present invention will be specifically described with Examples, but Examples are an embodiment of the invention, and the invention is not limited thereto.

[Test 1 for Confirming Usefulness of Cleaning with Guide Pipe Diameter Part being Provided to Cleaning Nozzle Member]

By using the cleaning device 100 which is provided with the cleaning nozzle member 21 as illustrated in FIG. 1, comparison of cleaning performance at the time of cleaning the object 5 is executed by comparing a case where the guide pipe diameter part 214 is provided in the cleaning nozzle member 21 as illustrated in FIG. 2 and a case where the guide pipe diameter part 214 is not provided in the cleaning nozzle member 21. Note that, as the object 5, the component (the pestle) of the pharmaceutical manufacturing machine (the tablet machine) to which the dirt of the pharmaceutical and the oil stain are stuck is used.

Example 1

<Preparation of Cleaning Fluid>
As the cleaning fluid, pure water was used.
<Preparation of Object>
The object 5 was prepared by melting ibuprofen and sticking the ibuprofen to the tip end portion and the side surface portion of the pestle, as the dirt of the pharmaceutical, and by applying machine oil to the side surface portion of the pestle with by using a brush, as the oil stain.
<Structure of Cleaning Nozzle Member 21>
As the cleaning nozzle member 21, a member was used, which is formed by including the large pipe diameter part 211, the small pipe diameter part 212, the conical pipe diameter part 213, and the guide pipe diameter part 214 forming the guide pipe flow passage S4 which is capable of entirely accommodating the object 5 (the pestle). The tip end portion of the object 5 (the pestle) was inserted into the conical pipe diameter part 213 of the cleaning nozzle member 21, the handle of the pestle was inserted into the guide pipe diameter part 214, and the object 5 (the pestle) was set into the cleaning nozzle member 21.

<Cleaning Operation>
The pure water was pressure-fed from the retention tank 3 into the large-diameter flow passage S1 of the large pipe diameter part 211 in the cleaning nozzle member 21 as the cleaning fluid 31 via the cleaning fluid feed port 211b in a state of being pressured with 0.40 MPa of pressure. At this time, the flow rate of the cleaning fluid 31 which is ejected via the conical flow passage S3 of the conical pipe diameter part 213 in the cleaning nozzle member 21 was set to be 40.0 L/min. Under the aforementioned conditions, the cleaning treatment was performed on the object 5 (the pestle) by using the pure water (pH=7.14). Note that, the temperature of the cleaning fluid 31 was set to be 25° C.

Comparative Example 1

The cleaning treatment was performed on the object 5 (the pestle) by using the pure water (pH=7.14) under the same conditions as Example 1 except for using the cleaning nozzle member which is not provided with the guide pipe diameter part for accommodating the object 5 (the pestle).
<Test Result>
In the above-described Example 1 and Comparative Example 1, the removability of the dirt of the pharmaceutical, and the oil stain, which are stuck to the object 5 (the pestle) was evaluated by visual check or touch.

In Example 1 in which the object 5 (the pestle) was cleaned by using the cleaning nozzle member 21 which is provided with the guide pipe diameter part 214, it was found that the dirt of the pharmaceutical and the oil stain which are stuck to the object 5 (the pestle) were completely removed by the cleaning treatment for 20 minutes.

On the other hand, in Comparative Example 1 in which the object 5 (the pestle) was cleaned by using the cleaning nozzle member which is not provided with the guide pipe diameter part for accommodating the object 5 (the pestle), it was found that the dirt of the pharmaceutical and the oil stain which are stuck to the object 5 (the pestle) were completely removed at the tip end portion of the object 5 (the pestle) for 20 minutes of cleaning time as same in Test Example 1, but were not completely removed on the side surface portion, and it takes 30 minutes to completely clean the entirety of the object 5 (the pestle).

[Test 2 for Confirming Usefulness of Cleaning with Guide Pipe Diameter Part being Provided to Cleaning Nozzle Member]

By using the cleaning device 100 which is provided with the cleaning nozzle member 21 as illustrated in FIG. 1, comparison of cleaning performance at the time of cleaning the object 5 was executed by comparing a case where the guide pipe diameter part 214 is provided in the cleaning nozzle member 21 as illustrated in FIG. 2 and a case where the guide pipe diameter part 214 is not provided in the cleaning nozzle member 21. Note that, as the object 5, an endoscopic surgical instrument to which the burned component is stuck was used.

Example 2

<Preparation of Cleaning Fluid>
As the cleaning fluid, a neutral enzymatic cleaning agent was used.

<Preparation of Object>

A pseudo blood was applied to the tip end portion and the side surface portion of the endoscopic surgical instrument, and a 25 W of soldering iron for an electronic component came in contact with the pseudo blood for 10 seconds to 20 seconds so as to prepare the object 5 to which the burned component is stuck.

<Structure of Cleaning Nozzle Member 21>

As the cleaning nozzle member 21, a member was used, which is formed by including the large pipe diameter part 211, the small pipe diameter part 212, the conical pipe diameter part 213, and the guide pipe diameter part 214 for accommodating the object 5 (the endoscopic surgical instrument). The tip end portion of the object 5 (the endoscopic surgical instrument) was inserted into the conical pipe diameter part 213 of the cleaning nozzle member 21, the handle of the endoscopic surgical instrument was inserted into the guide pipe diameter part 214, and the object 5 (the endoscopic surgical instrument) was set into the cleaning nozzle member 21.

<Cleaning Operation>

The pure water was pressure-fed from the retention tank 3 to the large-diameter flow passage S1 of the large pipe diameter part 211 in the cleaning nozzle member 21 as the cleaning fluid 31 via the cleaning fluid feed port 211b in a state of being pressured with 0.20 MPa of pressure. At this time, the flow rate of the cleaning fluid 31 which is ejected via the conical flow passage S3 of the conical pipe diameter part 213 in the cleaning nozzle member 21 was set to be 20.0 L/min. Under the aforementioned conditions, the cleaning treatment was performed on the object 5 (the endoscopic surgical instrument) by using the neutral enzymatic cleaning agent (pH=7.60). Note that, the temperature of the cleaning fluid 31 was set to be 50° C.

Comparative Example 2

The cleaning treatment was performed on the object 5 (the endoscopic surgical instrument) while adjusting the temperature to be 50° C. by using the cleaning agent which is diluted in 1 Wt % of a neutral enzymatic cleaning agent (pH=7.60) under the same conditions as Example 2 except for using the cleaning nozzle member which is not provided with the guide pipe diameter part for accommodating the object 5 (the endoscopic surgical instrument).

<Test Result>

In the above-described Example 2 and Comparative Example 2, the removability of the blood stain (burned component) in the object 5 (the endoscopic surgical instrument) was evaluated by visual check.

In Example 2 in which the object 5 (the endoscopic surgical instrument) was cleaned by using the cleaning nozzle member 21 which is provided with the guide pipe diameter part 214, it was found that the blood stain (burned component) which is stuck to the object 5 (the endoscopic surgical instrument) was completely removed by the cleaning treatment for 11 minutes.

On the other hand, in Comparative Example 2 in which the object 5 (the endoscopic surgical instrument) was cleaned by using the cleaning nozzle member which is not provided with the guide pipe diameter part for accommodating the object 5 (the endoscopic surgical instrument), it was found that residue of the blood stain still remains, that is, the blood stain (burned component) which is stuck to the object 5 (the endoscopic surgical instrument) was not completely removed at the tip end portion of the object 5 (the endoscopic surgical instrument) for 11 minutes of cleaning time as same in Example 2, and it took 15 minutes to completely clean the entirety of the object 5 (the endoscopic surgical instrument).

From the above-described test result, it was found that the object 5 was cleaned by using the cleaning nozzle member 21 which is provided with the guide pipe diameter part 214 corresponding to the shape of the object 5 (particularly, the pillar-like component), and thus it is possible to perform the cleaning treatment on the tip end portion and the side surface portion of the object 5 with high cleaning treatment capacity.

The cleaning devices 100, 200, and 300 according to the invention are preferably used for cleaning the constituent components for the pharmaceutical manufacturing machine, or the constituent components for medical instrument and the food manufacturing machine, and useful in a manufacturing field of pharmaceuticals and foods, or in a medical field.

Fourth Embodiment

Figure 5:
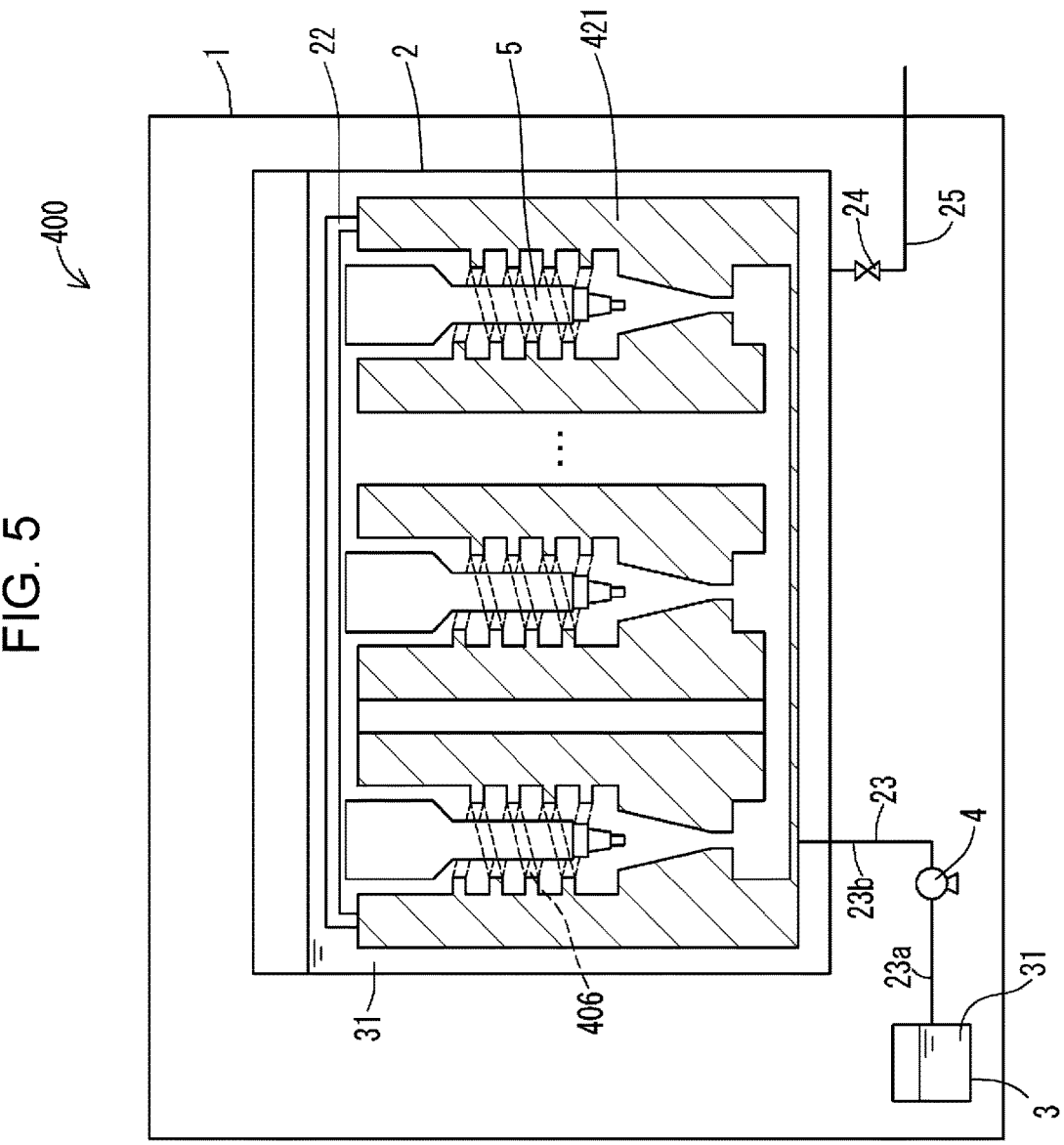
FIG. 5 is a diagram schematically illustrating a configuration of a cleaning device 400 according to a fourth embodiment of the invention.
Figure 6:
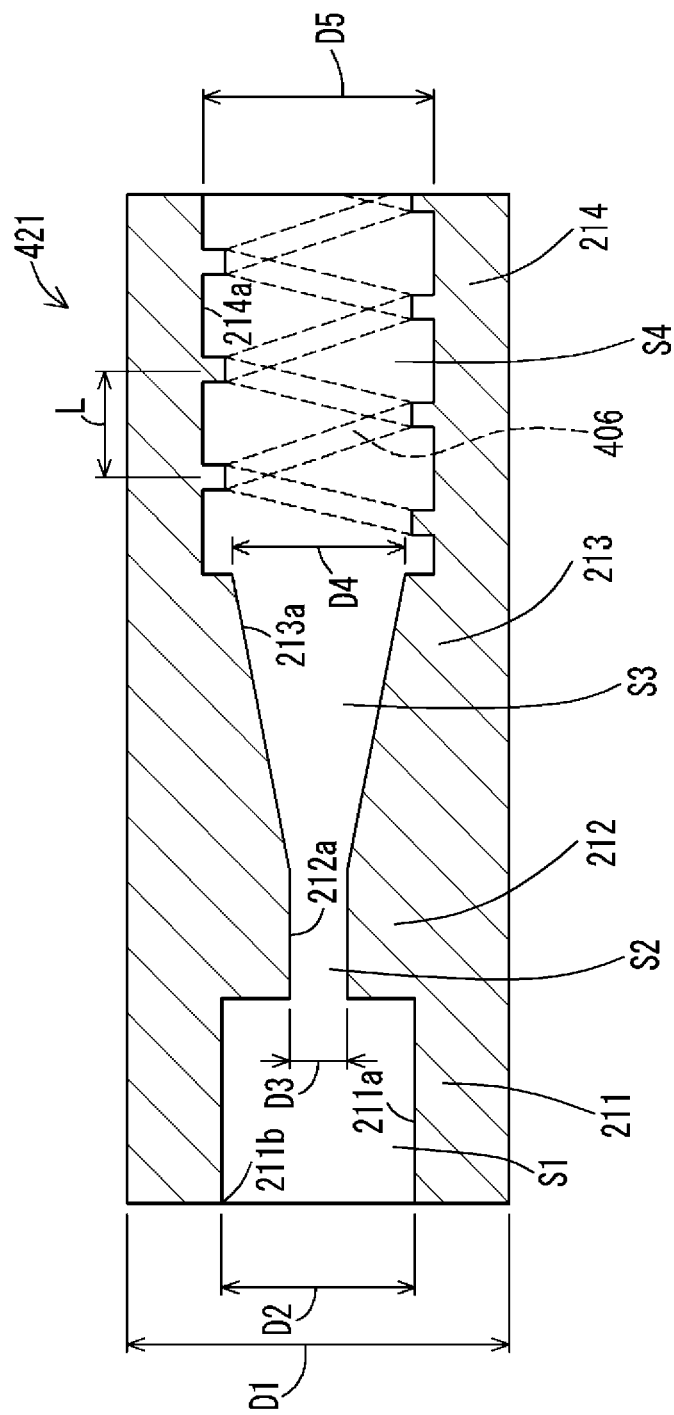
FIG. 6 is an enlarged diagram illustrating a configuration of a cleaning nozzle member 421.

FIG. 5 is a diagram schematically illustrating a configuration of a cleaning device 400 according to a fourth embodiment of the invention. FIG. 6 is an enlarged diagram illustrating a configuration of a cleaning nozzle member 421. The configuration of cleaning device 400 is similar to that of the cleaning device 100 in the first embodiment, and thus corresponding constituent elements are given the same reference numerals, and the description thereof will be omitted.

The cleaning device 400 is provided with a projecting portion 406 which is projected inwardly in an inner periphery portion of the guide pipe flow passage S4 in the guide pipe diameter part 214 of the cleaning nozzle member 421, and is projected in a direction perpendicular to the axial direction of the guide pipe flow passage S4.

Figure 7:
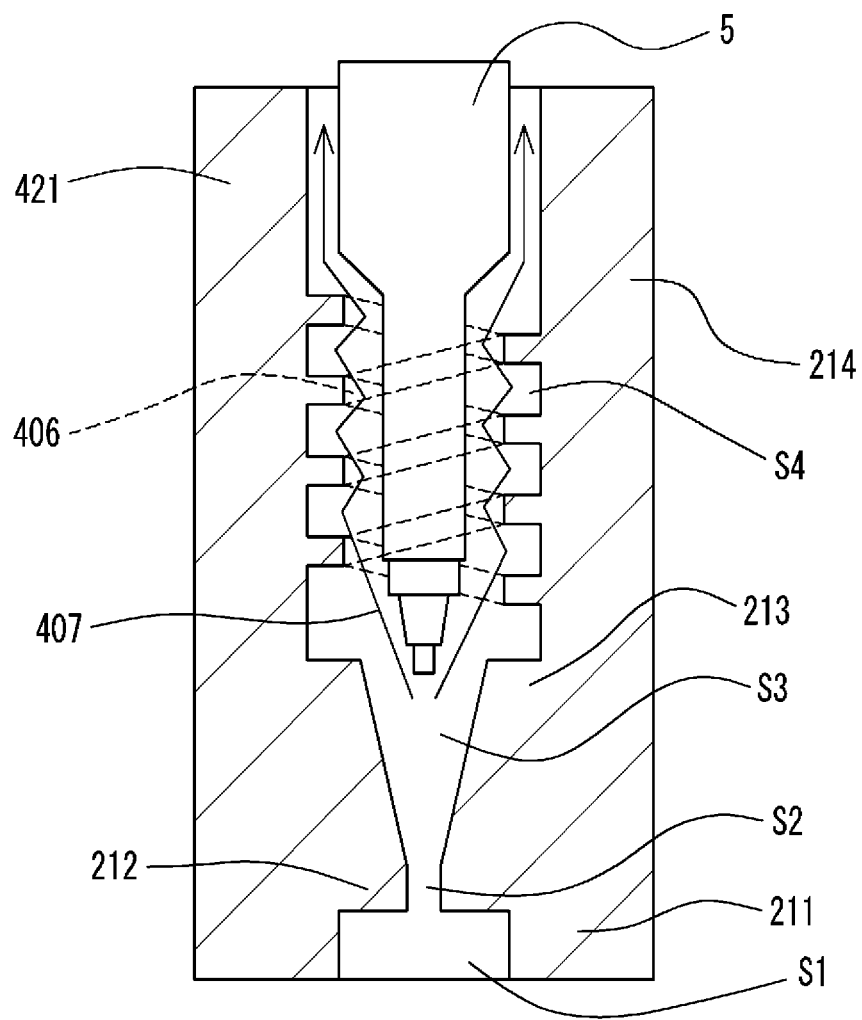
FIG. 7 is a diagram illustrated a state in which an object 5 is accommodated in a guide pipe diameter part 214 of the cleaning nozzle member 421.

FIG. 7 is a diagram illustrated a state in which an object 5 is retained in the guide pipe diameter part 214 of the cleaning nozzle member 421. Similar to the cleaning nozzle member 21 of the cleaning device 100 in the first embodiment, the cleaning nozzle member 421 is configured so as to clean the tip end and the side surface of the object 5 which is accommodated in the guide pipe diameter part 214 with the jet flow caused by the cleaning fluid 31 which is ejected to the guide pipe flow passage S4 via the conical flow passage S3.

In the embodiment, the projecting portion 406 is provided in the inner periphery portion of the guide pipe diameter part 214, and thus it is possible to guide a water flow 407 of the cleaning fluid 31 which is ejected to the guide pipe flow passage S4 not only to the direction parallel with the side surface of the object 5, but also to the direction perpendicular to the side surface of the object 5.

When providing the projecting portion 406, it is desired to set a pitch L between the projecting portions 406 in the axial direction of the guide pipe flow passage S4 to be about 5.0 mm to 20.0 mm. In addition, it is more desirable that the projecting portion 406 is provided so as to spirally extend in the axial direction of the guide pipe flow passage S4 as illustrated in FIG. 6, in other words, the projecting portion 406 is provided in the inner periphery portion of the guide pipe diameter part 214 so as to form a spiral groove.

With the pitch L being set to be within the aforementioned numerical range, it is possible to efficiently guide the jet flow, which flows into the direction parallel with the side surface of the object 5 of the cleaning fluid 31 which is ejected to the guide pipe flow passage S4 via the conical flow passage S3, to the direction perpendicular to the side surface of the object 5 as well by the projecting portion 406. With this, it is possible to impart the strong physical force to the side surface portion of the object 5.

Note that, the shape of projecting portion 406 which is provided in the inner periphery portion of the guide pipe diameter part 214 is not limited to a spiral shape, for example, the projecting portion 406 may extend in zigzag along the axial direction of the guide pipe flow passage S4, or the inner periphery portion of the guide pipe diameter part 214 may be formed of continuous irregularities along the axial direction of the guide pipe flow passage S4, that is, may be provided so as to have a wave form.

In addition, examples of the shape of cross-section of the projecting portion 406 include a semicircle, a square, a triangle, and the like. A method of forming the guide pipe diameter part 214 which includes such a projecting portion 406 includes forming by cutting out a cylindrical tube with a cutting drill for a trapezoidal thread, forming by using a 3D printer, and forming by bonding the spiral projecting portion 406 which is formed separately from the cleaning nozzle member 421 to the inner periphery surface 214a of the guide pipe diameter part 214 of the cleaning nozzle member 421.

As described above, according to the embodiment, in the cleaning nozzle member 421, the clearance between the inner periphery surface 214a of the guide pipe diameter part 214 and the outer surface of the object 5 is set to be about 2.0 mm to 10.0 mm, and the pitch L of the projecting portion 406, which is projected inwardly in an inner periphery portion of the guide pipe diameter part 214, and is projected in a direction perpendicular to the axial direction of the guide pipe flow passage S4, in the axial direction is set to be about 5.0 mm to 20.0 mm. Thus, it is possible to guide the jet flow into the guide pipe diameter part 214 without losing a physical force, which is caused by the jet flow of the cleaning fluid 31 which is ejected to the guide pipe flow passage S4 via the conical flow passage S3, working in a bus line direction into the cleaning tank 2, and it is possible to efficiently guide the jet flow which flows into the direction parallel with the side surface of the object 5 to the direction perpendicular to the side surface of the object 5 as well by the projecting portion 406. With this, it is possible to impart the strong physical force to the side surface portion of the object 5 as well, and thus it is possible to efficiently remove the dirt (the residue of the pharmaceutical, the oil, the grease, or the like) sticking to the side surface portion of the object 5 such as the component which constitute the pharmaceutical manufacturing machine, or the dirt (the burned component or the like) sticking to the side surface portion of the object 5 such as the medical instrument.

Fifth Embodiment

Figure 8:
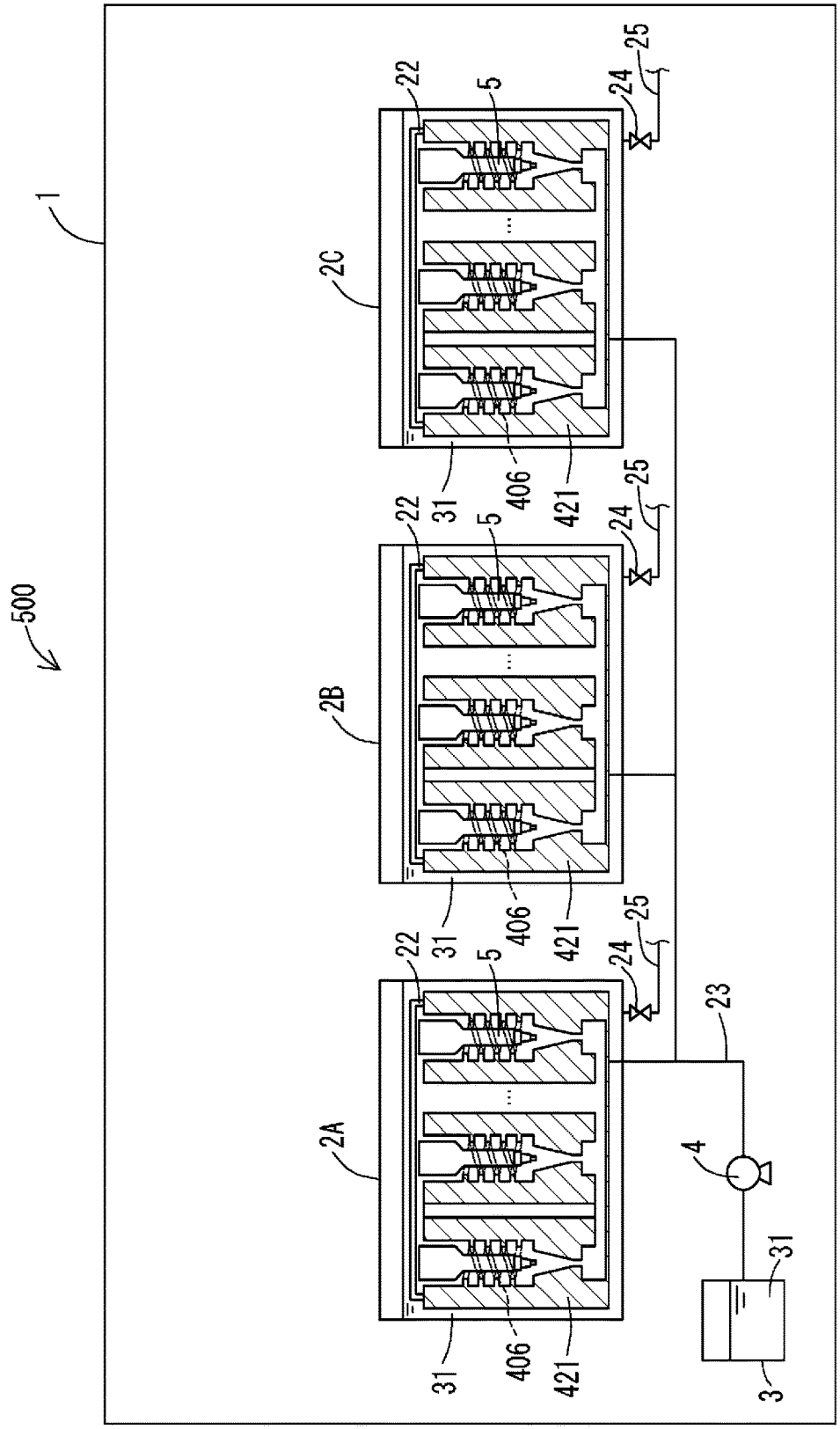
FIG. 8 is a diagram schematically illustrating a configuration of a cleaning device 500 according to a fifth embodiment of the invention.

FIG. 8 is a diagram schematically illustrating a configuration of a cleaning device 500 according to a fifth embodiment of the invention. The configuration of the cleaning device 500 is similar to that of the cleaning device 400 in the fourth embodiment, and thus corresponding constituent elements are given the same reference numerals, and the description thereof will be omitted.

In the cleaning device 500, the plurality of cleaning tanks 2A, 2B, and 2C which are formed in the same way as the cleaning tank 2 provided in the cleaning device 400 as described above are arranged in parallel. Each of the cleaning tanks 2A, 2B, and 2C is provided with a plurality of the cleaning nozzle members 421 similarly in the cleaning tank 2 provided in the cleaning device 400. FIG. 8 illustrates the configuration in which three cleaning tanks 2A, 2B, and 2C are arranged in parallel, but the number of the cleaning tanks is not limited thereto, for example, two cleaning tanks, or four or more of cleaning tanks may be arranged in parallel.

In the cleaning device 500 including the plurality of cleaning tanks 2A, 2B, and 2C which are arranged in parallel, it is possible to perform the cleaning treatment on the object 5 which is disposed in the guide pipe flow passage S4 by the physical force caused by ejecting the cleaning fluid 31 of which the speed becomes faster in the small-diameter flow passage S2 of each of the cleaning nozzle members 421 of each of the cleaning tanks 2A, 2B, and 2C. In such a cleaning device 500, it is possible to prevent the ejecting force of the cleaning fluid 31 from being deteriorated in each of the cleaning nozzle members 421 of each of the cleaning tanks 2A, 2B, and 2C, to efficiently guide the jet flow caused by the cleaning fluid 31 which is ejected to the guide pipe flow passage S4 to the direction perpendicular to the side surface of the object 5 by the projecting portion 406, and to perform the cleaning treatment on a plurality of the objects 5.

Sixth Embodiment

Figure 9:
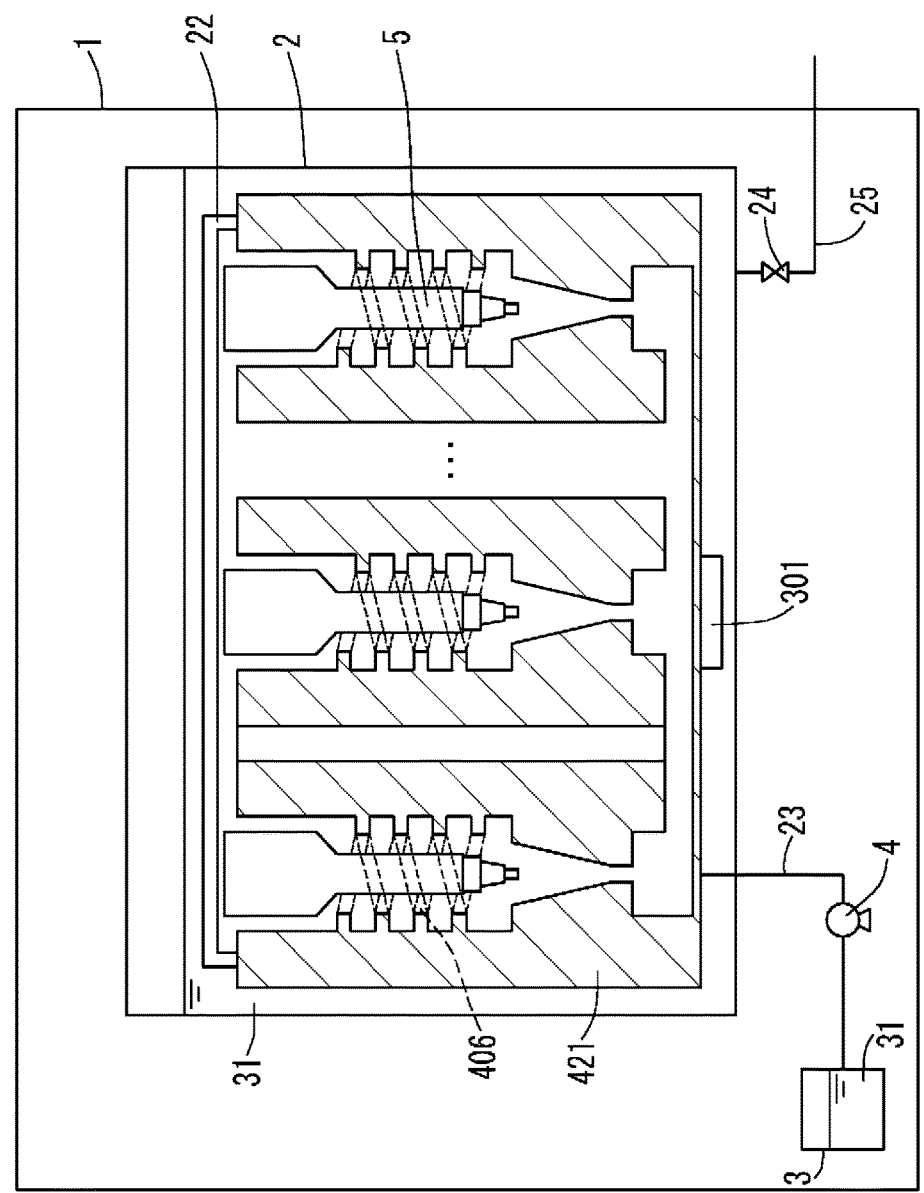
FIG. 9 is a diagram schematically illustrating a configuration of a cleaning device 600 according to a sixth embodiment of the invention.

FIG. 9 is a diagram schematically illustrating a configuration of a cleaning device 600 according to a sixth embodiment of the invention. The configuration of the cleaning device 600 is similar to that of the cleaning device 400 in the fourth embodiment, and thus corresponding constituent elements are given the same reference numerals, and the description thereof will be omitted.

The cleaning device 600 is configured to clean the object 5 by further imparting the ultrasonic vibration as a physical force to the above-described cleaning device 400.

The cleaning device 600 is formed of the cleaning tank 2 which is provided with the cleaning nozzle member 421 in the fourth embodiment, and the ultrasonic wave generating unit 301 provided in the cleaning device 300 in the third embodiment. The ultrasonic wave generating unit 301 is installed by coming in contact with the cleaning nozzle member 421, and generates ultrasonic waves when the object 5 is cleaned with the jet flow caused by the cleaning fluid 31.

Accordingly, in the cleaning device 600, in addition to the cleaning of the object 5 by ejecting the cleaning fluid 31 of which the speed becomes faster in the small-diameter flow passage S2 of the cleaning device 400 in the fourth embodiment to the object 5, it is possible to promote peeling off the dirt sticking to the surface of the object 5 by imparting the physical force caused by the ultrasonic vibration to the object 5, and thus it is possible to further improve the cleaning effect.

Herein below, the present invention will be specifically described with Examples, but Examples are an embodiment of the invention, and the invention is not limited thereto.

[Test 3 for Confirming Usefulness of Cleaning with Projecting Portion being Provided to Guide Pipe Diameter Part]

Further, by using the cleaning device 400 which is provided with the cleaning nozzle member 421 as illustrated in FIG. 5, comparison of cleaning performance at the time of cleaning the object 5 is executed by comparing a case where the projecting portion 406 is provided in the cleaning nozzle member 421 and a case where the projecting portion 406 is not provided in the cleaning nozzle member 421. Note that, as the object 5, the component (the pestle) of the pharmaceutical manufacturing machine (the tablet machine) to which the dirt of the pharmaceutical and the oil stain are stuck is used.

Example 3

<Preparation of Cleaning Fluid>
As the cleaning fluid, a neutral cleaning agent was used.
<Preparation of Object>
The object 5 was prepared by melting ibuprofen and sticking the tip end portion and the side surface portion of the pestle, as the dirt of the pharmaceutical, and by taking the grease such as ANDEROL by finger and applying it to the side surface portion of the pestle, as the grease stain.
<Structure of Cleaning Nozzle Member 421>
As the cleaning nozzle member 421, a member was used, which is formed by including the large pipe diameter part 211, the small pipe diameter part 212, the conical pipe diameter part 213, the guide pipe diameter part 214 forming the guide pipe flow passage S4 which is capable of entirely accommodating, and the object 5 (the pestle), and the projecting portion 406 which is provided in the inner periphery portion of the guide pipe diameter part 214. The tip end portion of the object 5 (the pestle) was inserted into the conical pipe diameter part 213 of the cleaning nozzle member 421, the handle of the pestle was inserted into the guide pipe diameter part 214, and the object 5 (the pestle) was set into the cleaning nozzle member 421.
<Cleaning Operation>
The neutral cleaning agent (pH=7.28) was pressure-fed from the retention tank 3 to the large-diameter flow passage S1 of the large pipe diameter part 211 in the cleaning nozzle member 421 as the cleaning fluid 31 via the cleaning fluid feed port 211b in a state of being pressured with 0.20 MPa of pressure. At this time, the flow rate of the cleaning fluid 31 which is ejected via the conical flow passage S3 of the conical pipe diameter part 213 in the cleaning nozzle member 421 was set to be 35.0 L/min. Under the aforementioned conditions, the cleaning treatment was performed on the object 5 (the pestle). Note that, the temperature of the cleaning fluid 31 was set to be 40° C.

Comparative Example 3

The cleaning treatment was performed on the object 5 (the pestle) by using the neutral cleaning agent (pH=7.28) under the same conditions as Example 3 except for using the cleaning nozzle member in which the guide pipe diameter part 214 not provided with the projecting portion 406.
<Test Result>
In the above-described Test Example 3 and Comparative Example 3, the removability of the dirt of the pharmaceutical and the grease stain which are stuck to the object 5 (the pestle) was evaluated by visual check or touch.
In Test Example 3 in which the object 5 (the pestle) was cleaned by using the cleaning nozzle member 421 in which the projecting portion 406 is provided in the guide pipe diameter part 214, it was found that the dirt of the pharmaceutical and the grease stain which are stuck to the object 5 (the pestle) were completely removed by the cleaning treatment for 30 minutes.
On the other hand, in Comparative Example 3 in which the object 5 (the pestle) was cleaned by using the cleaning nozzle member in which the projecting portion 406 is not provided in the guide pipe diameter part 214, it was found that, it took 60 minutes to completely clean the entirety of the object 5 (the pestle) including the dirt of the pharmaceutical and the grease stain which are stuck to the object 5 (the pestle) and the dirt on the side surface.

[Test 4 for Confirming Usefulness of Cleaning with Projecting Portion being Provided to Guide Pipe Diameter Part]
Further, by using the cleaning device 400 which is provided with the cleaning nozzle member 421 as illustrated in FIG. 5, comparison of cleaning performance at the time of cleaning the object 5 was executed by comparing a case where the projecting portion 406 is provided in the cleaning nozzle member 421 and a case where the projecting portion 406 is not provided in the cleaning nozzle member 421. Note that, as the object 5, the endoscopic surgical instrument to which the burned component is stuck was used.

Test Example 4

<Preparation of Cleaning Fluid>
As the cleaning fluid, the neutral enzymatic cleaning agent was used.
<Preparation of Object>
The pseudo blood was applied to the tip end portion and the side surface portion of the endoscopic surgical instrument, and a 25 W of soldering iron for an electronic component came in contact with the pseudo blood for 10 seconds to 20 seconds so as to prepare the object 5 to which the burned component is stuck.
<Structure of Cleaning Nozzle Member 421>
As the cleaning nozzle member 421, a member was used, which is formed by including the large pipe diameter part 211, the small pipe diameter part 212, the conical pipe diameter part 213, the guide pipe diameter part 214 for accommodating, the object 5 (the endoscopic surgical instrument), and the projecting portion 406 which is provided in the inner periphery portion of the guide pipe diameter part 214. The tip end portion of the object 5 (the endoscopic surgical instrument) was inserted into the conical pipe diameter part 213 of the cleaning nozzle member 421, the handle of the endoscopic surgical instrument was inserted into the guide pipe diameter part 214, and the object 5 (the endoscopic surgical instrument) was set into the cleaning nozzle member 421.
<Cleaning Operation>
The neutral enzymatic cleaning agent (pH=7.60) was pressure-fed from the retention tank 3 to the large-diameter flow passage S1 of the large pipe diameter part 211 in the cleaning nozzle member 421 as the cleaning fluid 31 via the cleaning fluid feed port 211b in a state of being pressured with 0.20 MPa of pressure. At this time, the flow rate of the cleaning fluid 31 which is ejected via the conical flow passage S3 of the conical pipe diameter part 213 in the cleaning nozzle member 421 was set to be 20.0 L/min. Under the aforementioned conditions, the cleaning treatment was performed on the object 5 (the endoscopic surgical instrument). Note that, the temperature of the cleaning fluid 31 was set to be 50° C.

Comparative Example 4

The cleaning treatment was performed on the object 5 (the endoscopic surgical instrument) while adjusting the temperature to be 50° C. by using the cleaning agent which is diluted in 1 wt % of a neutral enzymatic cleaning agent (pH=7.60) under the same conditions as Example 4 except for using the cleaning nozzle member in which the projecting portion 406 was not provided in the guide pipe diameter part 214.

<Test Result>

In the above-described Test Example 4 and Comparative Example 4, the removability of the blood stain (burned component) in the object 5 (the endoscopic surgical instrument) is evaluated by visual check.

In Test Example 4 in which the object 5 (the endoscopic surgical instrument) was cleaned by using the cleaning nozzle member 421 in which the projecting portion 406 is provided in the guide pipe diameter part 214, it was found that the blood stain (burned component) which is stuck to the object 5 (the endoscopic surgical instrument) was completely removed by the cleaning treatment for 9 minutes.

On the other hand, in Comparative Example 4 in which the object 5 (the endoscopic surgical instrument) was cleaned by using the cleaning nozzle member in which the projecting portion 406 is not provided in the guide pipe diameter part 214, it was found that it took 11 minutes to completely clean the entirety of the object 5 (the endoscopic surgical instrument) including the blood stain (burned component) which is stuck to the object 5 (the endoscopic surgical instrument).

From the above-described test result, it was found that the object 5 was cleaned by using the cleaning nozzle member 421 which is provided with the guide pipe diameter part 214 corresponding to the shape of the object 5 (particularly, the pillar-like component) and in which the projecting portion 406 is provided in the guide pipe diameter part 214, and thus it is possible to perform the cleaning treatment on the tip end portion and the side surface portion of the object 5 with high cleaning treatment capacity.

Seventh Embodiment

Figure 10:
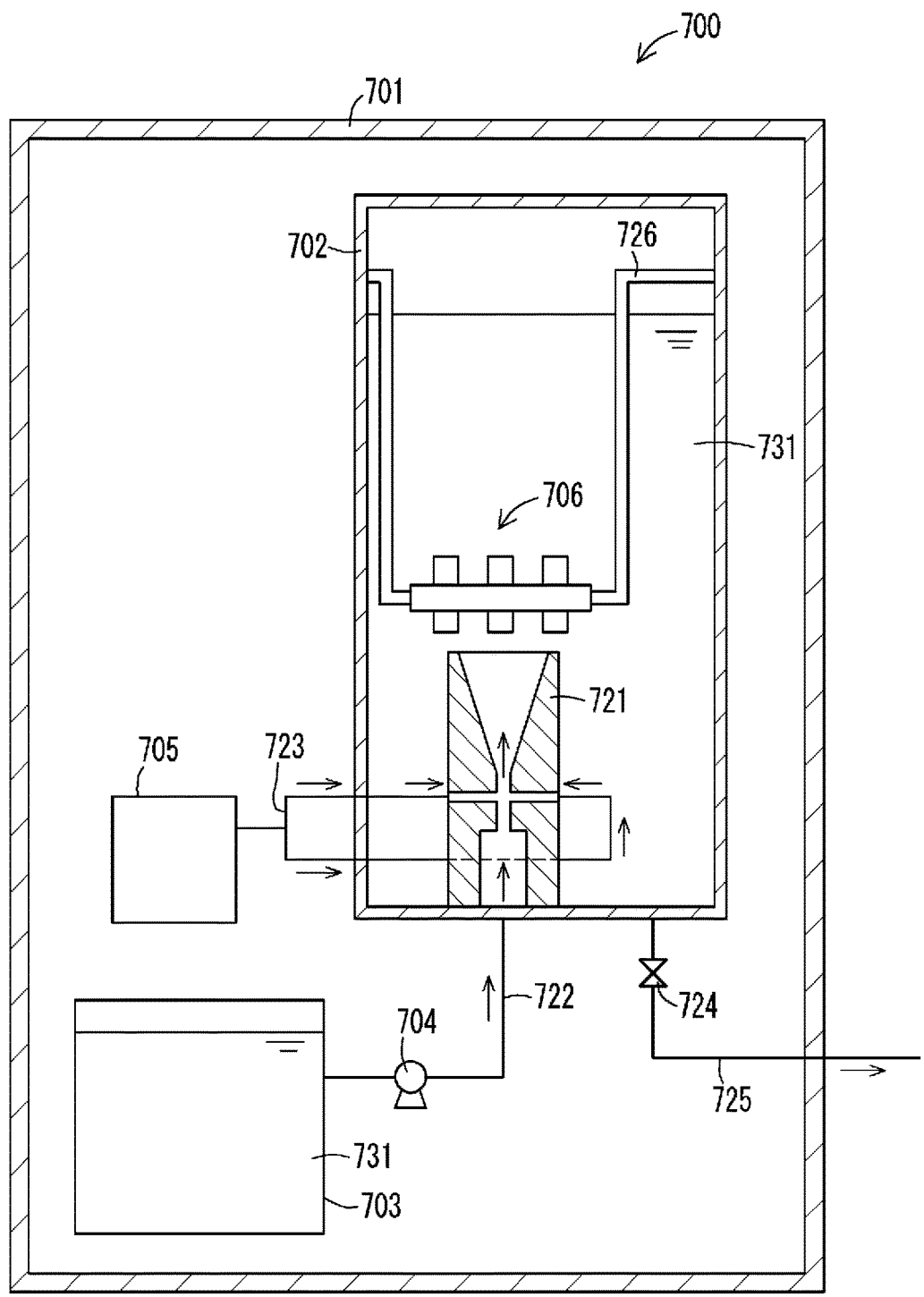
FIG. 10 is a diagram schematically illustrating a configuration of a cleaning device 700 according to a seventh embodiment of the invention.

FIG. 10 is a diagram schematically illustrating a configuration of a cleaning device 700 according to a seventh embodiment of the invention. The cleaning method of the invention can be realized by using this cleaning device 700.

The cleaning device 700 is an apparatus for cleaning the object such as the component for constituting the pharmaceutical manufacturing machine, and an apparatus for removing dirt such as residues of a pharmaceutical (powder) which are stuck to the component for constituting the pharmaceutical manufacturing machine by a physical force and a chemical force.

Examples of an object 706 such as a component constituting a pharmaceutical manufacturing machine in the cleaning device 700 which performs a cleaning treatment include a mortar, a pestle, and a rotary board of a tablet machine which compression-molds a tablet for a pharmaceutical, and a rotary board of a grinder. The residues of a cured granulated pharmaceutical are stuck to the mortar, the pestle, and the rotary board.

The cleaning device 700 in the embodiment is configured so as to remove residues of the pharmaceutical by using a jet flow occurring in a cleaning nozzle 721 which serves as a fluid ejecting nozzle, in a state where the object 706 of the pharmaceutical manufacturing machine to which the residues of the pharmaceutical are stuck is immersed in a cleaning fluid 731 in the cleaning tank 702.

The cleaning device 700 is provided with a case 701 which becomes an outline. In the case 701, the cleaning tank 702, a retention tank 703, a liquid feeding pump 704, and a gas cylinder 705 are retained. Here, the gas cylinder 705 may be disposed in the outside of the case 701. In the cleaning device 700 in the embodiment, a cleaning fluid retention portion is formed of the retention tank 703, a cleaning fluid discharge portion is formed of the liquid feeding pump 704, and the gas retention portion is formed of the gas cylinder 705.

In the cleaning tank 702, the cleaning nozzle 721 for imparting the jet flow to the object 706 is provided. The object 706 is fixed by the fixing jig 726 so as to efficiently impart the jet flow. The cleaning nozzle 721 may be fixed, or may be provided with a mechanism which is movable to clean the object 706 without deviation. In addition, a plurality of the cleaning nozzles 721 may be provided in the cleaning tank 702. Further, a mechanism for driving the object 706 with respect to the cleaning nozzle 721 may be provided so as to efficiently impart the jet flow to the object 706.

The cleaning tank 702 and the retention tank 703 are connected to each other via the cleaning fluid feed pipe 722. The liquid feeding pump 704 is connected to the cleaning fluid feed pipe 722. The cleaning fluid 731 which is retained in the retention tank 703 is pressure-fed by driving the liquid feeding pump 704 in a state where the inside of the cleaning fluid feed pipe 722 is pressured, and supplied into the cleaning tank 702. In addition, liquid feeding ports of the cleaning tank 702 and the liquid feeding pump 704 may be connected to each other by using a pipe, and the cleaning fluid 731 may be circulated via the liquid feeding pump 704. In this way, the cleaning fluid 731, in a state of being pressured, which is supplied into the cleaning tank 702 is configured so as to be ejected from the cleaning nozzle 721. The cleaning fluid 731 which is ejected as described above causes the jet flow to occur in the cleaning tank 702, and is maintained in a state of being retained in the cleaning tank 702.

As the cleaning fluid 731, for example, the pure water is desirable; however, ozone water or an organic acid such as an oxalic acid, a citric acid, a formic acid, a lactic acid, glycolic acid, or acetic acid may be exemplified. The cleaning fluid 731 does not remain in the pharmaceutical manufacturing machine after being used, and is excellent in safety, and thus is desirable from the viewpoint of validation. Particularly, when removing metal stains such as insoluble calcium salt or magnesium salt, and an iron oxide, it is preferable to use an organic acid.

The gas cylinder 705 retains the gas fluid in a pressured state, and pressure-feeds the retained gas fluid by opening a valve which is installed in the gas cylinder 705. The cleaning nozzle 721 and the gas cylinder 705 are connected to each other via the gas feed pipe 723, and the gas fluid flows into the cleaning fluid 731 which is supplied into the cleaning tank 702 and a part thereof is dissolved by using an effect by the venturi tube described below. As described above, the cleaning fluid 731 (the gas-liquid mixture fluid) into which the gas fluid flows is ejected from the cleaning nozzle 721. Examples of the gas fluid which flows into the cleaning fluid 731 include nitrogen, carbon dioxide, and the like. The gas fluid which flows into the cleaning fluid 731 has no corrosion problem and is excellent in safety, and thus is desirable from the viewpoint of validation. Particularly, when mixing the carbon dioxide into the gas fluid, carbonated water is made, the chemical force for removing the metal stain is promoted, and thus the pure water is enough to be used as the cleaning fluid 731, and from the viewpoint of convenience for operating the apparatus and cost benefits, the carbon dioxide is preferably used.

In addition, a drain pipe 725 is connected to a bottom of the cleaning tank 702, and a drain valve 724 which opens and closes a flow passage in the drain pipe 725 is connected to the drain pipe 725. After completing the cleaning treatment in the cleaning device 700, the used cleaning fluid 731 in the cleaning tank 702 can be discarded to the outside of the apparatus. It is possible to discard the used cleaning fluid 731 which is retained in the cleaning tank 702 to the outside of the apparatus by opening the drain valve 724 such that the used cleaning fluid 731 flows through the inside of the drain pipe 725.

Figure 11:
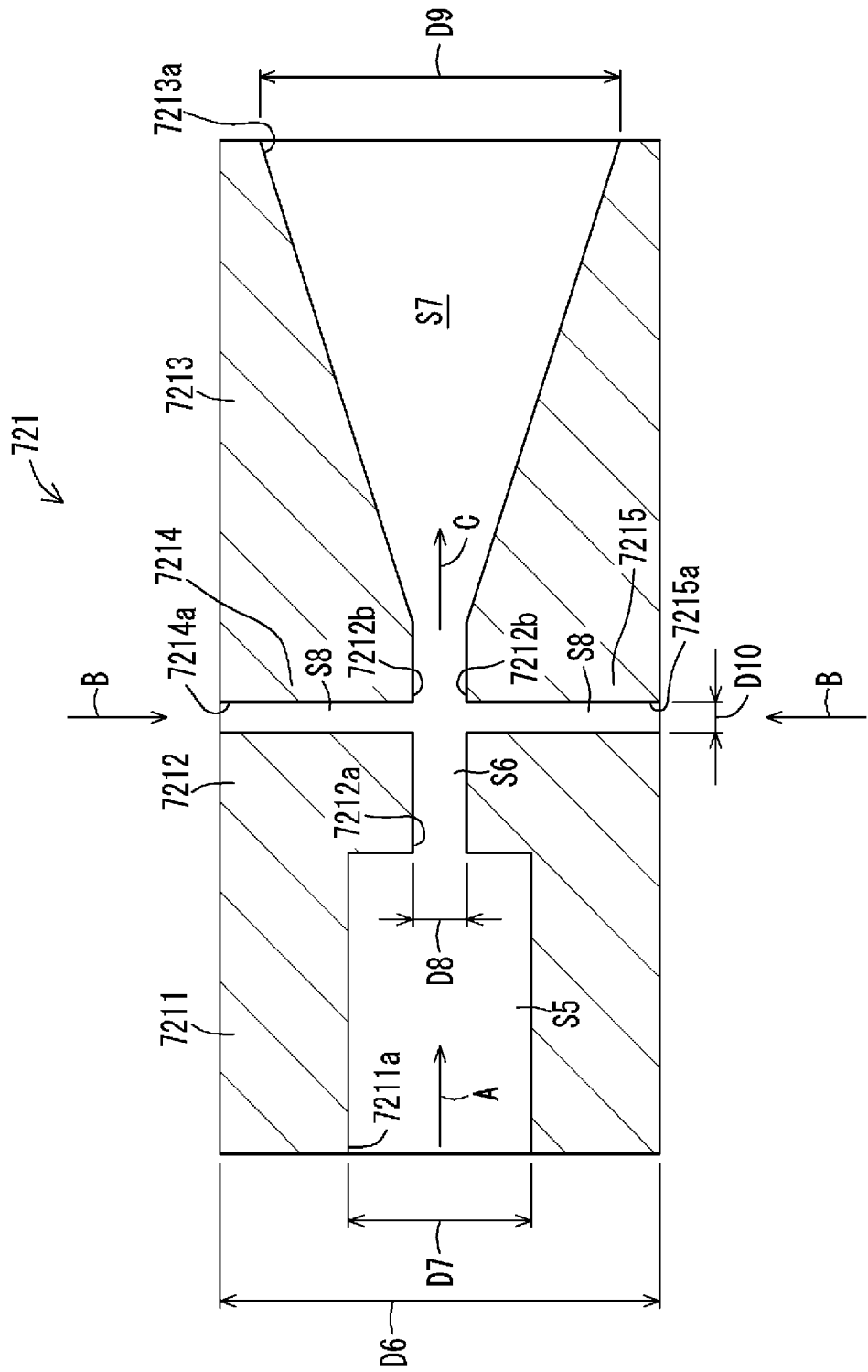
FIG. 11 is an enlarged diagram illustrating a configuration of a cleaning nozzle 721.

FIG. 11 is an enlarged diagram illustrating a configuration of a cleaning nozzle 721, and a state where a gas-liquid mixture fluid obtained by mixing the cleaning fluid 731 with the gas fluid is ejected from the cleaning nozzle 721 will be described with reference to FIG. 11.

The cleaning nozzle 721 is provided in the cleaning tank 702, is connected to the retention tank 703 in which the cleaning fluid 731 is retained via the cleaning fluid feed pipe 722, is connected to the gas cylinder 705 which is filled with the gas fluid via the gas feed pipe 723, and ejects the gas-liquid mixture fluid which is obtained by mixing the cleaning fluid 731 with the gas fluid into the cleaning tank 702. The cleaning nozzle 721 is formed by including a cleaning fluid feed portion 7211, a throttle portion 7212 which is a gas-liquid mixture portion, an ejecting portion 7213, and gas feed portions 7214 and 7215.

The gas feed portions 7214 and 7215 include a gas feed flow passage S8 to which the gas fluid discharged from the gas cylinder 705 is supplied, and are provided with gas feed holes 7214a and 7215a for causing the gas fluid which is discharged from the gas cylinder 705 and flows into the gas feed pipe 723 to flow through the inside of the gas feed flow passage S8. That is, the gas fluid which is discharged from the gas cylinder 705 and flows into the gas feed pipe 723 is supplied into the gas feed flow passage S8 of the gas feed portions 7214 and 7215 via the gas feed holes 7214a and 7215a. In the embodiment, the gas feed portions 7214 and 7215 are formed into a cylindrical shape, the gas feed holes 7214a and 7215a are defined by the cylindrical inner periphery surface of the gas feed portions 7214 and 7215, and communicate with an inner space of the gas feed pipe 723. An inner diameter D10 of the gas feed holes 7214a and 7215a is, for example, 6.0 mm.

The cleaning fluid feed portion 7211 includes a cleaning fluid feed flow passage S5 to which the cleaning fluid 731 which is discharged from the retention tank 703 by the liquid feeding pump 704 is supplied, and is provided with a cleaning fluid feed hole 7211a for causing the cleaning fluid 731 which is discharged from the retention tank 703 and flows into the cleaning fluid feed pipe 722 to flow through the inside of the cleaning fluid feed flow passage S5. That is, the cleaning fluid 731 which is discharged from the retention tank 703 and flows into the cleaning fluid feed pipe 722 is supplied into the cleaning fluid feed flow passage S5 of the cleaning fluid feed portion 7211 via the cleaning fluid feed hole 7211a. In the embodiment, the cleaning fluid feed portion 7211 is formed into a cylindrical shape, the cleaning fluid feed hole 7211a is defined by the cylindrical inner periphery surface of the cleaning fluid feed portion 7211, and communicates with the inner space of the cleaning fluid feed pipe 722. An outer diameter D6 of the cleaning fluid feed portion 7211 is, for example, 30.0 mm, and an inner diameter D7 (that is, the inner diameter of the cleaning fluid feed hole 7211a) is, for example, 20.0 mm.

The throttle portion 7212 is connected to the gas feed portions 7214 and 7215, and the cleaning fluid feed portion 7211. The throttle portion 7212 communicates with the gas feed flow passage S8 of the gas feed portions 7214 and 7215 and the cleaning fluid feed flow passage S5 of the cleaning fluid feed portion 7211, includes a gas-liquid mixture flow passage S6 obtained by mixing the gas fluid and the cleaning fluid 731, and is provided with a throttle hole 7212a for causing the cleaning fluid 731 which flows into the cleaning fluid feed flow passage S5 to flow through the inside of the gas-liquid mixture flow passage S6, and a gas inflow hole 7212b for causing the gas fluid which flows into the gas feed flow passage S8 to flow through the inside of the gas-liquid mixture flow passage S6. That is, the cleaning fluid 731 which flows into the cleaning fluid feed flow passage S5 of the cleaning fluid feed portion 7211 flows into the gas-liquid mixture flow passage S6 of the throttle portion 7212 via throttle hole 7212a, and the gas fluid which flows into the gas feed flow passage S8 of the gas feed portions 7214 and 7215 flows into the gas-liquid mixture flow passage S6 of the throttle portion 7212 via the gas inflow hole 7212b. In the embodiment, the throttle portion 7212 is formed into a cylindrical shape, the throttle hole 7212a is defined by the cylindrical inner periphery surface of the throttle portion 7212, and communicates with the cleaning fluid feed flow passage S5. In addition, the gas inflow hole 7212b is formed on the inner peripheral wall surface of the throttle portion 7212 so as to face the gas-liquid mixture flow passage S6, and communicates with the gas feed flow passage S8.

Further, in the embodiment, the flow passage cross-sectional area of the gas-liquid mixture flow passage S6 of the throttle portion 7212 is set to be smaller than the flow passage cross-sectional area of the cleaning fluid feed flow passage S5 of the cleaning fluid feed portion 7211, and the flow passage cross-sectional area of a mixed fluid-passing flow passage S7 of the ejecting portion 7213 described below. When comparing the flow passage cross-sectional area of the gas-liquid mixture flow passage S6 with the flow passage cross-sectional area of the cleaning fluid feed flow passage S5, the inner diameter D7 of the cleaning fluid feed hole 7211a for defining the flow passage cross-sectional area of the cleaning fluid feed flow passage S5 is 20.0 mm as described above, whereas an inner diameter D8 of the throttle hole 7212a for defining the flow passage cross-sectional area of the gas-liquid mixture flow passage S6 is, for example, 6.0 mm. Note that, in the throttle portion 7212, the inner diameter of the gas inflow hole 7212b is the same as the inner diameter D10 of the gas feed holes 7214a and 7215a.

The ejecting portion 7213 is connected to the throttle portion 7212. The ejecting portion 7213 includes the mixed fluid-passing flow passage S7 which communicates with the gas-liquid mixture flow passage S6 of the throttle portion 7212, and through which the gas-liquid mixture fluid which is mixed in the gas-liquid mixture flow passage S6 flows, and is provided with an ejecting hole 7213a for causing the gas-liquid mixture fluid which flows into the mixed fluid-passing flow passage S7 to be ejected into the cleaning tank 702. That is, the gas-liquid mixture fluid which flows into the gas-liquid mixture flow passage S6 of the throttle portion 7212, flows into the mixed fluid-passing flow passage S7 of the ejecting portion 7213, and the gas-liquid mixture fluid which flows into the mixed fluid-passing flow passage S7 is ejected into the cleaning tank 702 via the ejecting hole 7213a. In the embodiment, the mixed fluid-passing flow passage S7 in the ejecting portion 7213 is formed into a truncated cone shape, an inner diameter of an opening on the flow-in side communicating with the throttle hole 7212a of the ejecting portion 7213 is the same as the inner diameter D8 of the throttle hole 7212a, and the inner diameter of the opening on the side to which the gas-liquid mixture fluid of the ejecting portion 7213 is ejected, that is, an inner diameter D9 of the ejecting hole 7213a is, for example, 13.0 mm.

In the cleaning nozzle 721, the cleaning fluid feed portion 7211, the throttle portion 7212, and the ejecting portion 7213 are configured such that the cleaning fluid feed hole 7211a, the throttle hole 7212a, and the ejecting hole 7213a are integrally formed by being continued in this order on the same center axis line (herein below, referred to as a "first center axis line"). In addition, in the cleaning nozzle 721, the two gas feed portions 7214 and 7215 are configured such that the gas feed holes 7214a and 7215a are integrally formed with the throttle portion 7212 by being arranged on a second center axis line which is perpendicular to the first center axis line.

In the cleaning device 700 formed as described above, in the cleaning nozzle 721, which is provided in the cleaning tank 702, the gas fluid which is discharged from the gas cylinder 705 and flows in a direction of arrow B so as to be supplied into the gas feed flow passage S8 of the gas feed portions 7214 and 7215 via the gas feed holes 7214a and 7215a, and the cleaning fluid 731, which is discharged from the retention tank 703 and flows in a direction of an arrow A so as to be supplied into the cleaning fluid feed flow passage S5 of the cleaning fluid feed portion 7211 via the cleaning fluid feed hole 7211a, are mixed in the gas-liquid mixture flow passage S6 of the throttle portion 7212, and the gas-liquid mixture fluid which is mixed as above flows in a direction of an arrow C and is ejected from the ejecting hole 7213a into the cleaning tank 702 in the mixed fluid-passing flow passage S7 of the ejecting portion 7213. In this way, the gas-liquid mixture fluid which is obtained by mixing the cleaning fluid 731 and the gas fluid is ejected from the cleaning nozzle 721 so as to clean the object 706, and thus the cleaning device 700 of the embodiment has high cleaning capability, thereby efficiently removing residues of the pharmaceutical which are stuck to the component (the object 706) constituting the pharmaceutical manufacturing machine.

In addition, as the gas fluid which is discharged from the gas cylinder 705, the carbon dioxide is preferably used. With this, in addition to the physical force which is caused by ejection of the gas-liquid mixture fluid, it is possible to clean the object 706 by using the chemical force of the carbon dioxide, and thus it is possible to efficiently remove the residues of the pharmaceutical which are stuck to the component (the object 706) constituting the pharmaceutical manufacturing machine.

Further, in the cleaning nozzle 721, it is preferable that the flow passage cross-sectional area of the gas-liquid mixture flow passage S6 of the throttle portion 7212 is set to be smaller than the flow passage cross-sectional area of the cleaning fluid feed flow passage S5 of the cleaning fluid feed portion 7211, and the flow passage cross-sectional area of the mixed fluid-passing flow passage S7 of the ejecting portion 7213. Such a cleaning nozzle 721 has a so-called venturi tube structure in which the flow passage cross-sectional area of the throttle portion 7212 which is positioned between the cleaning fluid feed portion 7211 corresponding to an inlet to which the cleaning fluid 731 is supplied, and the ejecting portion 7213 corresponding to an outlet from which the gas-liquid mixture fluid is ejected is reduced. In the cleaning nozzle 721 having such a venturi tube structure, some of the pressure energy of the fluid is replaced with the speed energy, and thus it is possible to eject the gas-liquid mixture fluid which is obtained by mixing the cleaning fluid 731 having the flow rate accelerated in the throttle portion 7212 of which the flow passage cross-sectional area is reduced, and the gas fluid from the ejecting hole 7213a of the ejecting portion 7213. As a result, it is possible to efficiently remove the residues of the pharmaceutical which are stuck to the component (the object 706) constituting the pharmaceutical manufacturing machine.

Further, in the cleaning nozzle 721, the flow passage cross-sectional area of the gas-liquid mixture flow passage S6 of the throttle portion 7212 is set such that the cavitation is caused by the gas-liquid mixture fluid which flows into the mixed fluid-passing flow passage S7 of the ejecting portion 7213. With such a cavitation, the gas-liquid mixture fluid becomes a fluid containing minute bubbles. By cleaning the object 706 with the gas-liquid mixture fluid containing the bubbles due to the cavitation, it is possible to clean the object 706 by imparting the impact generated when the bubbles are collapsed to the object 706, and thus it is possible to efficiently remove the residues of the pharmaceutical which are stuck to the component (the object 706) constituting the pharmaceutical manufacturing machine.

Moreover, in the embodiment, the flow rate of the gas-liquid mixture fluid which is ejected from the ejecting hole 7213a of the ejecting portion 7213 in the cleaning nozzle 721 is preferably equal to or greater than 20 L/min. With this, since it is possible to eject the high flow rate of the gas-liquid mixture fluid to the object 706, the object 706 can be cleaned by the strong physical force, and thus it is possible to efficiently remove the residues of the pharmaceutical which are stuck to the component (the object 706) constituting the pharmaceutical manufacturing machine.

Further, the temperature of the gas-liquid mixture fluid which is ejected from the ejecting hole 7213a of the ejecting portion 7213 in the cleaning nozzle 721 may be adjusted by heating using the heating means such as the heat element on the upstream side from the throttle hole 7212a, for example, in the cleaning fluid feed hole 7211a so as to be, for example, 20° C. to 50° C. Alternatively, in a case where the temperature of the cleaning fluid 731 is high due to the pressure by the liquid feeding pump 704, the temperature may be adjusted by circulating cool water in the outside of the cleaning tank 702. With this, it is possible to further improve the cleaning effect.

Eighth Embodiment

Figure 12:
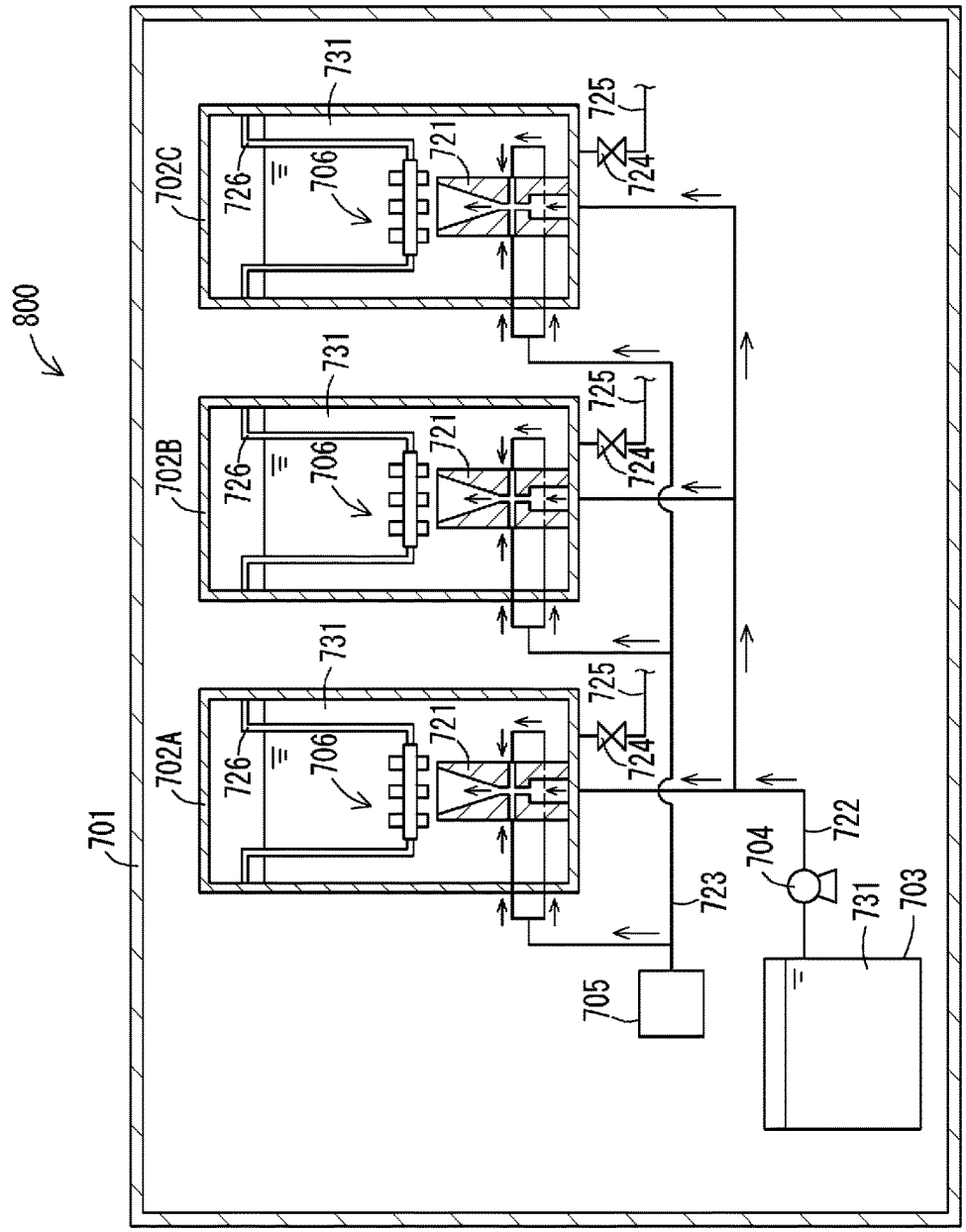
FIG. 12 is a diagram schematically illustrating a configuration of a cleaning device 800 according to an eighth embodiment of the invention.

FIG. 12 is a diagram schematically illustrating a configuration of a cleaning device 800 according to an eighth embodiment of the invention. The configuration of the cleaning device 800 is similar to that of the cleaning device 700 in the seventh embodiment, and thus corresponding constituent elements are given the same reference numerals, and the description thereof will be omitted.

In the cleaning device 800, a plurality of cleaning tanks 702A, 702B, and 702C which are formed in the same way as the cleaning tank 702 provided in the cleaning device 700 as described above are arranged in parallel. Each of the cleaning tanks 702A, 702B, and 702C is provided with the cleaning nozzle 721 similarly in the cleaning tank 702. FIG. 12 illustrates a configuration in which three cleaning tanks 702A, 702B, and 702C are arranged in parallel, but the number of the cleaning tanks is not limited thereto, for example, two cleaning tanks, or four or more of cleaning tanks may be arranged in parallel.

Each of the cleaning tanks 702A, 702B, and 702C and the retention tank 703 are connected to each other via the cleaning fluid feed pipe 722. The liquid feeding pump 704 is connected to the cleaning fluid feed pipe 722. The cleaning fluid 731 retained in the retention tank 703 is pressure-fed by driving the liquid feeding pump 704 in a state where the inside of the cleaning fluid feed pipe 722 is pressured, and supplied into each of the cleaning tanks 702A, 702B, and 702C. In addition, a configuration such that liquid feeding ports in each of the cleaning tanks 702A, 702B, and 702C, and the liquid feeding pump 704 are connected to each other by using a pipe, and the cleaning fluid is circulated via the liquid feeding pump 704 may be employed.

In addition, the cleaning nozzle 721 which is provided in each of the cleaning tanks 702A, 702B, and 702C and the gas cylinder 705 are connected to each other via the gas feed pipe 723, and the gas fluid flows into the cleaning fluid 731 which is supplied into each of the cleaning tanks 702A, 702B, and 702C and a part thereof is dissolved by using an effect by the venturi tube described below. As described above, the gas-liquid mixture fluid obtained by mixing the gas fluid with the cleaning fluid 731 is ejected from each of the cleaning nozzles 721.

In the cleaning device 800 including the plurality of the cleaning tanks 702A, 702B, and 702C which are arranged in parallel, in each of the cleaning tanks 702A, 702B, and 702C, it is possible to perform the cleaning treatment on the object 706 with the physical force which is caused by ejection of the gas-liquid mixture fluid from the cleaning nozzle 721, and the chemical force which is caused by using the gas-liquid mixture fluid obtained by mixing the cleaning fluid 731 with the gas fluid as described above. In such a cleaning device 800, it is possible to prevent the ejecting force of the gas-liquid mixture fluid from the cleaning nozzle 721 from being deteriorated in each of the cleaning tanks 702A, 702B, and 702C, and to perform the cleaning treatment on a plurality of the objects 706.

Ninth Embodiment

Figure 13:
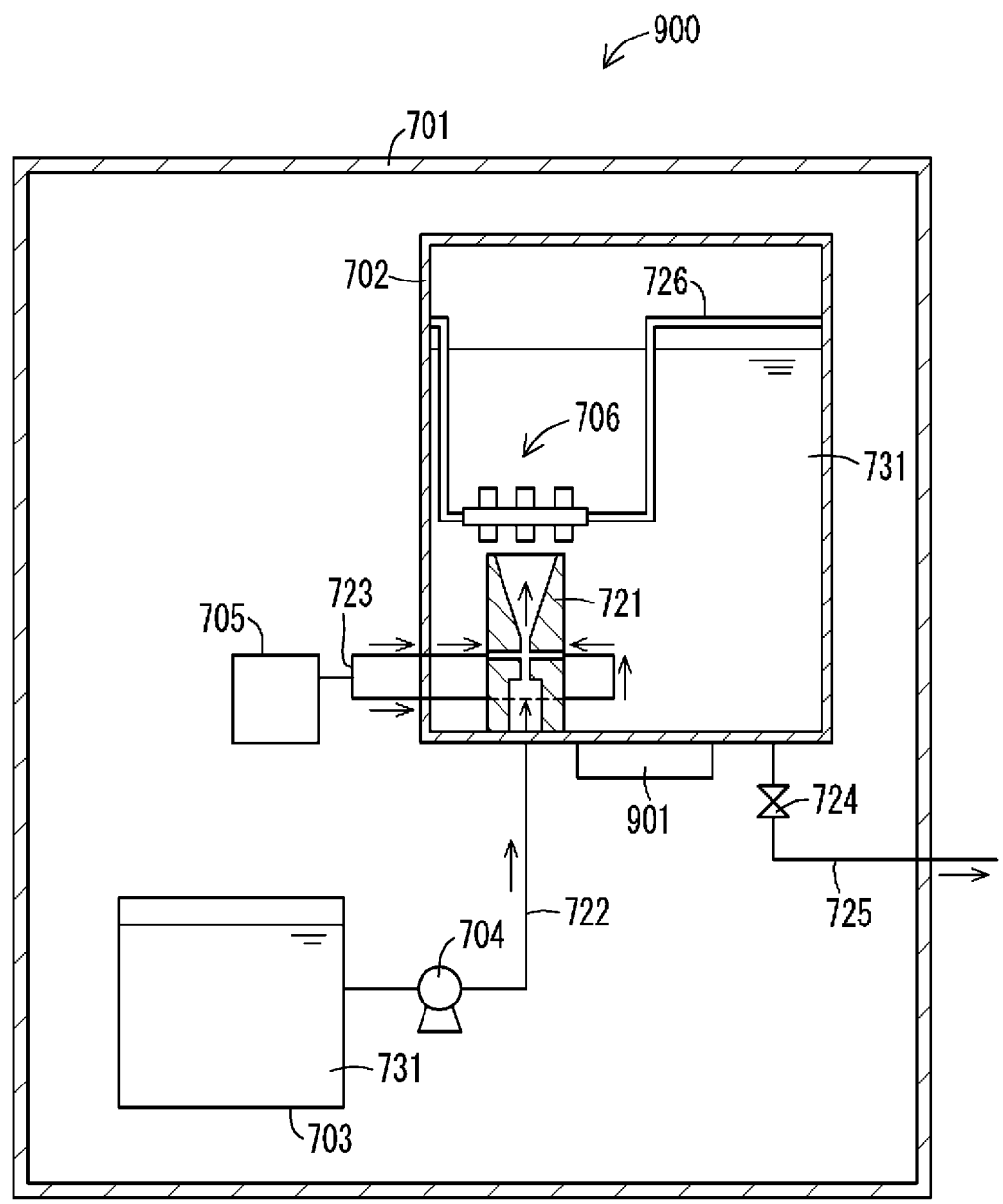
FIG. 13 is a diagram schematically illustrating a configuration of a cleaning device 900 according to a ninth embodiment of the invention.

FIG. 13 is a diagram schematically illustrating a configuration of a cleaning device 900 according to a ninth embodiment of the invention. The configuration of the cleaning device 900 is similar to that of the cleaning device 700 in the seventh embodiment, and thus corresponding constituent elements are given the same reference numerals, and the description thereof will be omitted.

The cleaning device 900 is configured to clean the object 706 by further imparting the ultrasonic vibration as a physical force to the above-described cleaning device 700.

The cleaning device 900 is formed by including the cleaning tank 702 which is provided in the cleaning device 700 and an ultrasonic wave generating unit 901. In the cleaning device 900, the ultrasonic wave is generated by the ultrasonic wave generating unit 901 in a state where the object 706 is immersed in the cleaning fluid 731 retained in the cleaning tank 702. With this, it is possible to impart the physical force caused by the ultrasonic vibration with respect to the object 706 which is immersed in the cleaning fluid 731 retained in the cleaning tank 702, and thus it is possible to promote peeling off the dirt sticking to the surface of the object 706.

In the cleaning device 900, in addition to the cleaning of the object 706 by ejecting the gas-liquid mixture fluid, in which the gas fluid of the cleaning device 700 according to the seventh embodiment is melted, to the object 706, it is possible to impart the physical force caused by the ultrasonic vibration to the object 6, and thus it is possible to further improve the cleaning effect.

Hereinbelow, the present invention will be specifically described with Examples, but Examples are an embodiment of the invention, and the invention is not limited thereto.

[Test for Confirming Usefulness of Cleaning with Gas-Liquid Mixture Fluid in which Carbon Dioxide is Mixed]

By using the cleaning device 700 which is provided with the cleaning nozzle 721 as illustrated in FIG. 10, comparison of cleaning performance was executed by comparing a case where the object is cleaned by using the gas-liquid mixture fluid obtained by mixing the cleaning fluid with the carbon dioxide and a case where the object is cleaned by using the cleaning fluid without the carbon dioxide. In addition, as the object, the component (the rotary board) of the pharmaceutical manufacturing machine (the grinder) to which the residues of the pharmaceutical are stuck was used.

Example 5

<Preparation of Cleaning Fluid>
As the cleaning fluid, the pure water was used.
<Feed of Gas Fluid>
As the gas fluid, the carbon dioxide was supplied to the throttle portion 7212 of the cleaning nozzle 721 by using a cylinder, as the gas cylinder 705, which is filled with carbon dioxide.
<Cleaning Operation>
The pure water was pressure-fed from the retention tank 703 into the cleaning fluid feed flow passage S5 of the cleaning fluid feed portion 7211 in the cleaning nozzle 721 as the cleaning fluid via the cleaning fluid feed hole 7211a in a state of being pressured with 0.06 MPa of pressure. In addition, the carbon dioxide was supplied into the gas feed flow passage S8 of the gas feed portions 7214 and 7215 in the cleaning nozzle 721 as the gas fluid via the gas feed holes 7214a and 7215a, at the flow rate of 1 L/min. At this time, the flow rate of the gas-liquid mixture fluid which is ejected from the ejecting hole 7213a of the ejecting portion 7213 in the cleaning nozzle 721 was set to be 20.0 L/min. Under the aforementioned conditions, the cleaning treatment was performed on the component of the pharmaceutical manufacturing machine for 40 minutes by using the gas-liquid mixture fluid (pH=5.4) obtained by mixing the pure water with the carbon dioxide, which is generated in the cleaning nozzle 721. Note that, the temperature of the cleaning fluid (the pure water) was set to be 25° C.

Comparative Example 5

The cleaning treatment was performed on the component of the pharmaceutical manufacturing machine for 40 minutes by using the pure water (pH=7.14) under the same conditions as Example 5 except that the gas fluid is not supplied into the gas feed flow passage S8 of the gas feed portions 7214 and 7215 in the cleaning nozzle 721.
<Test Result>
In the above-described Example 5 and Comparative Example 5, the removability of the residues of the pharmaceutical in the component (the object) of the pharmaceutical manufacturing machine was evaluated by visual check.

In Example 5 in which the object is cleaned by using the gas-liquid mixture fluid obtained by mixing the pure water with the carbon dioxide, it was found that the residues of the pharmaceutical which are stuck to the object were completely removed.

On the other hand, in Comparative Example 5 in which the object is cleaned by using the pure water without mixing with the carbon dioxide, it was found that the residues of the pharmaceutical which are stuck to the object were not completely removed, and the cleaning was not sufficiently performed.

From the above-described test result, it was found that the object was cleaned by using the gas-liquid mixture fluid obtained by mixing the cleaning fluid (pure water) with the gas fluid (the carbon dioxide), and thus it was possible to perform the cleaning treatment with high cleaning treatment capacity.

[Test for Confirming Usefulness of Cleaning According to Difference of Flow Rate]

By using the cleaning device 700 which is provided with the cleaning nozzle 721 as illustrated in FIG. 10, comparison of cleaning performance was executed by cleaning the object at four different flow rates of 10.0 L/min, 15.0 L/min, 20.0 L/min, and 25.0 L/min of the gas-liquid mixture fluids (the fluid obtained by mixing the pure water with the carbon dioxide) which are ejected from the cleaning nozzle 721. In addition, as the object, the component (the pestle and the mortar) of the pharmaceutical manufacturing machine (the tablet machine) to which the residues of the pharmaceutical are stuck was used.

Example 6

<Preparation of Cleaning Fluid>

As the cleaning fluid, the pure water was used.

<Feed of Gas Fluid>

As the gas fluid, the carbon dioxide was supplied to the throttle portion 7212 of the cleaning nozzle 721 by using a cylinder, as the gas cylinder 705, which is filled with carbon dioxide.

<Cleaning Operation>

The pure water was pressure-fed from the retention tank 703 into the cleaning fluid feed flow passage S5 of the cleaning fluid feed portion 7211 in the cleaning nozzle 721 as the cleaning fluid via the cleaning fluid feed hole 7211a in a state of being pressured with 0.01 MPa of pressure. In addition, the carbon dioxide was supplied into the gas feed flow passage S8 of the gas feed portions 7214 and 7215 in the cleaning nozzle 721 as the gas fluid via the gas feed holes 7214a and 7215a, at the flow rate of 1 L/min. At this time, the flow rate of the gas-liquid mixture fluid which is ejected from the ejecting hole 7213a of the ejecting portion 7213 in the cleaning nozzle 721 was set to be 10.0 L/min. Under the aforementioned conditions, the cleaning treatment was performed on the component of the pharmaceutical manufacturing machine for 60 minutes by using the gas-liquid mixture fluid (pH=5.4) obtained by mixing the pure water with the carbon dioxide, which is generated in the cleaning nozzle 721. Note that, the temperature of the cleaning fluid (the pure water) was set to be 25° C.

Example 7

The pure water was pressure-fed from the retention tank 703 into the cleaning fluid feed flow passage S5 of the cleaning fluid feed portion 7211 in the cleaning nozzle 721 as the cleaning fluid via the cleaning fluid feed hole 7211a in a state of being pressured with 0.03 MPa of pressure. In addition, the carbon dioxide was supplied into the gas feed flow passage S8 of the gas feed portions 7214 and 7215 in the cleaning nozzle 721 as the gas fluid via the gas feed holes 7214a and 7215a, at the flow rate of 1 L/min. At this time, the flow rate of the gas-liquid mixture fluid which is ejected from the ejecting hole 7213a of the ejecting portion 7213 in the cleaning nozzle 721 was set to be 15.0 L/min. By setting other conditions to be the same as in Example 6, the cleaning treatment was performed on the component of the pharmaceutical manufacturing machine for 60 minutes by using the gas-liquid mixture fluid (pH=5.4) obtained by mixing the pure water with the carbon dioxide.

Example 8

The pure water was pressure-fed from the retention tank 703 into the cleaning fluid feed flow passage S5 of the cleaning fluid feed portion 7211 in the cleaning nozzle 721 as the cleaning fluid via the cleaning fluid feed hole 7211a in a state of being pressured with 0.06 MPa of pressure. In addition, the carbon dioxide was supplied into the gas feed flow passage S8 of the gas feed portions 7214 and 7215 in the cleaning nozzle 721 as the gas fluid via the gas feed holes 7214a and 7215a, at the flow rate of 1 L/min. At this time, the flow rate of the gas-liquid mixture fluid which is ejected from the ejecting hole 7213a of the ejecting portion 7213 in the cleaning nozzle 721 was set to be 20.0 L/min. By setting other conditions to be the same as in Example 6, the cleaning treatment was performed on the component of the pharmaceutical manufacturing machine for 60 minutes by using the gas-liquid mixture fluid (pH=5.4) obtained by mixing the pure water with the carbon dioxide.

Example 9

The pure water was pressure-fed from the retention tank 703 into the cleaning fluid feed flow passage S5 of the cleaning fluid feed portion 7211 in the cleaning nozzle 721 as the cleaning fluid via the cleaning fluid feed hole 7211a in a state of being pressured with 0.10 MPa of pressure. In addition, the carbon dioxide was supplied into the gas feed flow passage S8 of the gas feed portions 7214 and 7215 in the cleaning nozzle 721 as the gas fluid via the gas feed holes 7214a and 7215a, at the flow rate of 1 L/min. At this time, the flow rate of the gas-liquid mixture fluid which is ejected from the ejecting hole 7213a of the ejecting portion 7213 in the cleaning nozzle 721 was set to be 25.0 L/min. By setting other conditions to be the same as in Example 6, the cleaning treatment was performed on the component of the pharmaceutical manufacturing machine for 60 minutes by using the gas-liquid mixture fluid (pH=5.4) obtained by mixing the pure water with the carbon dioxide.

<Test Result>

In Examples 6 to 9 described above, the removability of the residues of the pharmaceutical in the component of the pharmaceutical manufacturing machine was evaluated by visual check.

In Example 6 in which the object is cleaned by ejecting the gas-liquid mixture fluid obtained by mixing the pure water with the carbon dioxide at the flow rate of 10.0 L/min, a portion in which the residues of the pharmaceutical sticking to the object are not removed is found, but does not cause any practical problems.

In Example 7 in which the object is cleaned by ejecting the gas-liquid mixture fluid obtained by mixing the pure water with the carbon dioxide at the flow rate of 15.0 L/min, it was found that although the residues of the pharmaceutical which are stuck to the object were almost removed, some residual still existed, but it did not cause any practical problems. In addition, in Example 7, the effect of removing the residues of the pharmaceutical was higher than that in Example 6.

In Example 8 in which the object is cleaned by ejecting the gas-liquid mixture fluid obtained by mixing the pure water with the carbon dioxide at the flow rate of 20.0 L/min, it was found that the residues of the pharmaceutical which are stuck to the object were completely removed.

In Example 9 in which the object is cleaned by ejecting the gas-liquid mixture fluid obtained by mixing the pure water with the carbon dioxide at the flow rate of 25.0 L/min, it was found that the residues of the pharmaceutical which are stuck to the object were completely removed.

From the above-described test result, it is found that the effect of removing the residues of the pharmaceutical becomes higher by ejecting the gas-liquid mixture fluid which is obtained by mixing the cleaning fluid (the pure water) with the gas fluid (the carbon dioxide) at the flow rate of 20.0 L/min or greater.

The invention may be embodied in other various forms without departing from its spirit or main features. Accordingly, the embodiments described above are merely examples in all aspects, and the scope of the invention is described in claims, and thus the invention is not limited to the contents of the specification. Further, modifications and changes which belong to the claims are all within the scope of the present invention.

REFERENCE SIGNS LIST 1, 701: case
2, 702: cleaning tank
3, 703: retention tank
4, 704: liquid feeding pump
5, 706: object
406: projecting portion
407: water flow
21, 421: cleaning nozzle member
22: fixing jig
23, 722: cleaning fluid feed pipe
24, 724: drain valve
25, 725: drain pipe
31, 731: cleaning fluid
100, 200, 300, 400, 500, 600, 700, 800, and 900: cleaning device
211: large pipe diameter part
212: small pipe diameter part
213: conical pipe diameter part
214: guide pipe diameter part
301: ultrasonic wave generating unit
705: gas cylinder
721: cleaning nozzle
723: gas feed pipe
726: fixing jig
7211: cleaning fluid feed portion
7212: throttle portion
7213: ejecting portion
7214, 7215: gas feed portion
901: ultrasonic wave generating unit

The invention claimed is:

1. A cleaning device comprising:
a cleaning fluid retention portion which retains a cleaning fluid for cleaning an object;
a cleaning tank which is capable of accommodating the cleaning fluid;
a cleaning portion which ejects the cleaning fluid in the cleaning tank; and
a cleaning fluid discharge portion which is connected to the cleaning fluid retention portion, and discharges the cleaning fluid retained in the cleaning fluid retention portion to the cleaning portion in a pressured state,
wherein the cleaning portion includes
a first flow passage which is connected to the cleaning fluid discharge portion, and to which the cleaning fluid which is pressure-fed by the cleaning fluid discharge portion is supplied,
a second flow passage which is continued to a downstream end of the first flow passage, and of which a flow passage cross-sectional area is smaller than that of the first flow passage,
a third flow passage which is continued to a downstream end of the second flow passage, and of which a flow passage cross-sectional area becomes gradually larger as being separated from the second flow passage, and
an accommodating space which is continued to a downstream end of the third flow passage, is capable of accommodating the object, and is opened to the outside.

2. The cleaning device according to claim 1,
wherein a size of the accommodating space is sufficient for accommodating the entirety of the object.

3. The cleaning device according to claim 1,
wherein the first flow passage is formed into a right cylinder shape,
wherein the second flow passage is formed into a right cylinder shape having an outer diameter which is smaller than an outer diameter of the first flow passage, and
wherein the third flow passage is formed into a truncated cone shape having an outer diameter at an upstream end thereof which is equivalent to the outer diameter of the second flow passage, and an outer diameter at a downstream end thereof which is larger than the outer diameter of the second flow passage.

4. The cleaning device according to claim 1,
wherein the accommodating space is formed into a right cylinder shape having an outer diameter which is the same or substantially the same as an outer diameter of the third flow passage at the downstream end.

5. The cleaning device according to claim 4,
wherein the cleaning portion is provided with a projecting portion which is projected inwardly in an inner periphery portion which forms the accommodating space.

6. The cleaning device according to claim 1,
wherein the flow passage cross-sectional area of the second flow passage is determined such that the cleaning fluid which flows in the third flow passage becomes a cleaning fluid containing minute bubbles caused by cavitation.

7. A cleaning device comprising:
a cleaning tank which is capable of accommodating an object;
a cleaning fluid retention portion which retains a cleaning fluid for cleaning the object;
a cleaning fluid discharge portion which is connected to the cleaning fluid retention portion, and pressure-feeds the cleaning fluid retained in the cleaning fluid retention portion in a pressured state;
a gas retention portion which retains a gas fluid in a pressured state, and is capable of pressure-feeding the gas fluid; and
a fluid ejecting nozzle which is provided in the cleaning tank,
wherein the fluid ejecting nozzle includes
at least one gas feed portion which is connected to the gas retention portion via a gas-passing pipe, and includes a gas feed flow passage to which the gas fluid which is pressure-fed from the gas retention portion is supplied, a cleaning fluid feed portion which is connected to the cleaning fluid discharge portion via a cleaning fluid-passing pipe, and includes a cleaning fluid feed flow passage to which the cleaning fluid which is pressure-fed by the cleaning fluid discharge portion is supplied, a gas-liquid mixture portion which is connected to the at least one gas feed portion and the cleaning fluid feed portion, and includes a gas-liquid mixture flow passage in which the gas fluid which is pressure-fed from the gas feed flow passage and the cleaning fluid which is pressure-fed from the cleaning fluid feed flow passage are mixed with each other, and an ejecting portion which is connected to the gas-liquid mixture portion, includes a mixed fluid-passing flow passage in which the gas-liquid mixture fluid mixed in the gas-liquid mixture flow passage flows, and ejects the gas-liquid mixture fluid from the mixed fluid-passing flow passage, and wherein a flow passage cross-sectional area of the gas-liquid mixture flow passage is smaller than a flow passage cross-sectional area of a flow passage connected to an end on an upstream side of the gas-liquid mixture flow passage and a flow passage cross-sectional area of a flow passage connected to an end on a downstream side of the gas-liquid mixture flow passage.

8. The cleaning device according to claim 7, wherein a flow rate of the gas-liquid mixture fluid which is ejected from the ejecting portion is equal to or greater than 20 L/min.

9. The cleaning device according to claim 7, wherein the gas fluid is carbon dioxide.

10. The cleaning device according to claim 7, wherein the flow passage cross-sectional area of the gas-liquid mixture flow passage is smaller than the flow passage cross-sectional areas of the cleaning fluid feed flow passage and the mixed fluid-passing flow passage.

11. The cleaning device according to claim 10, wherein the flow passage cross-sectional area of the gas-liquid mixture flow passage is set such that the gas-liquid mixture fluid flowing into the mixed fluid-passing flow passage becomes a fluid containing minute bubbles caused by cavitation.

12. The cleaning device according to claim 7, wherein the at least one gas feed portion is provided with a gas inflow hole that causes the gas fluid to flow through the inside of the gas liquid mixture passage.

13. The cleaning device according to claim 12, wherein the at least one gas feed portion comprises two gas feed portions, and the two gas feed portions are configured so that respective gas inflow holes are arranged on a center axis line perpendicular to a center axis line of the fluid ejecting nozzle.

14. The cleaning device according to claim 7, wherein the ejecting portion includes an ejecting hole from which the gas-liquid mixture fluid in the gas-liquid mixture flow passage is ejected, and a flow passage cross-sectional area of the gas-liquid mixture flow passage increases toward the ejecting hole.

* * * * *